United States Patent
Ebright et al.

(10) Patent No.: US 9,243,039 B2
(45) Date of Patent: Jan. 26, 2016

(54) BIPARTITE INHIBITORS OF BACTERIAL RNA POLYMERASE: SAL-TARGET-INHIBITOR/NUCLEOSIDE-ANALOG-INHIBITOR CONJUGATES

(71) Applicant: Rutgers, The State University of New Jersey, New Brunswick, NJ (US)

(72) Inventors: Richard H. Ebright, New Brunswick, NJ (US); Yu Feng, New Brunswick, NJ (US); Yu Zhang, New Brunswick, NJ (US); Yon Ebright, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 14/104,935

(22) Filed: Dec. 12, 2013

(65) Prior Publication Data

US 2014/0162940 A1  Jun. 12, 2014

Related U.S. Application Data

(60) Provisional application No. 61/736,479, filed on Dec. 12, 2012.

(51) Int. Cl.
*A01N 37/18* (2006.01)
*A61K 38/04* (2006.01)
*A61K 38/12* (2006.01)
*C07K 11/02* (2006.01)

(52) U.S. Cl.
CPC ..................................... *C07K 11/02* (2013.01)

(58) Field of Classification Search
CPC .... A61K 47/48338; C12Q 1/18; C07K 11/02; C07K 1/1077
See application file for complete search history.

(56) References Cited

U.S. PATENT DOCUMENTS 5,919,926 A  7/1999  Fenical et al.
2014/0162939 A1  6/2014  Ebright et al.

FOREIGN PATENT DOCUMENTS

WO  WO 2007089310 A1 * 8/2007

OTHER PUBLICATIONS

Anstee et al., "Inhibition of bacterial RNA polymerases: peptide metabolites from the cultures of Streptomyces sp", *J. Nat. Prod.* 60, 858-861 (1997).
Chopra, "Bacterial RNA polymerase: a promising target for the discovery of new antimicrobial agents", *Curr. Opin. Investig. Drugs* 8, 600-607 (2007).
Darst, "New inhibitors targeting bacterial RNA polymerase", *Trends Biochem. Sci.* 29 (4), 159-162 (2004).
Ho et al., "Structures of RNA polymerase-antibiotic complexes", *Curr. Opin. Struct. Biol.* 19, 715-723 (2009).
Srivastava et al., :New Target for Inhibition of Bacterial RNA Polymerase: "Switch Region", *Curr. Opin. Microbiol.* 14, 532-543 (2011).
Trischman et al., "Salinamides A and B: anti-inflammatory depsipeptides frm a marine streptomycete", *J. Am. Chem. Soc.* 116, 757-758 (1994).
Trischman et al., "Salinamides: anti-inflammatory depsipeptides from a marine streptomycete", *J. Org. Chem.* 64, 1145-1150 (1999).
Villain-Guillot et al., "Progress in targeting bacterial transcription", *Drug. Discov. Today* 12 (5/6), 200-208 (2007).

* cited by examiner

*Primary Examiner* — Marcela M Cordero Garcia
*Assistant Examiner* — Kaipeen Yang
(74) *Attorney, Agent, or Firm* — Viksnins Harris & Padys PLLP

(57) ABSTRACT

The invention provides compounds of formula (I):

$$X\text{-}\alpha\text{-}Y \qquad (I)$$

wherein X, Y, and a have any of the values defined in the specification and salts thereof. The compounds are inhibitors of bacterial RNA polymerase.

30 Claims, 7 Drawing Sheets

A

| dataset | Eco RNAP | Eco RNAP-Sal |
|---|---|---|
| space group | P2(1)2(1)2(1) | P2(1)2(1)2(1) |
| resolution range | 50.00-3.90 Å (3.97-3.90 Å) | 50.00-3.90 Å (3.97-3.90 Å) |
| completeness | 0.997 (0.996) | 0.998 (0.997) |
| mean I/σ | 13.2 (1.8) | 15.5 (1.5) |
| Rmerge | 0.115 (0.625) | 0.118 (0.891) |
| Rwork | 0.276 | 0.286 |
| Rfree | 0.325 | 0.325 |
| PDB code | 4MEY | 4MEX |

B

C

BIPARTITE INHIBITORS OF BACTERIAL RNA POLYMERASE: SAL-TARGET-INHIBITOR/NUCLEOSIDE-ANALOG-INHIBITOR CONJUGATES

PRIORITY OF INVENTION

This application claims priority from U.S. Provisional Application No. 61/736,479, filed 12 Dec. 2012; the entire content of this provisional application is hereby incorporated herein by reference.

STATEMENT OF GOVERNMENT SUPPORT

This invention was made with government support under AI072766, AI104660, and GM041376 awarded by the National Institutes of Health. The government has certain rights in the invention.

BACKGROUND

Bacterial infectious diseases kill 100,000 persons each year in the US and 11 million persons each year worldwide, representing nearly a fifth of deaths each year worldwide (Heron et al., *Final Data for* 2006. *National Vital Statistics Reports, Vol.* 57 (Centers for Disease Control and Prevention, Atlanta Ga.) and World Health Organization (2008) *The Global Burden of Disease:* 2004 *Update* (World Health Organization, Geneva)). In the US, hospital-acquired bacterial infections strike 2 million persons each year, resulting in 90,000 deaths and an estimated $30 billion in medical costs (Klevins et al., (2007) Estimating health care-associated infections and deaths in U.S. hospitals. *Public Health Reports,* 122, 160-166; Scott, R. (2009) *The direct medical costs of healthcare-associated infections in U.S. hospitals and benefits of prevention* (Centers for Disease Control and Prevention, Atlanta Ga.)). Worldwide, the bacterial infectious disease tuberculosis kills nearly 2 million persons each year. One third of the world's population currently is infected with tuberculosis, and the World Health Organization projects that there will be nearly 1 billion new infections by 2020, 200 million of which will result in serious illness, and 35 million of which will result in death. Bacterial infectious diseases also are potential instruments of biowarfare and bioterrorism.

For six decades, antibiotics have been a bulwark against bacterial infectious diseases. This bulwark is failing due to the appearance of resistant bacterial strains. For all major bacterial pathogens, strains resistant to at least one current antibiotic have arisen. For several bacterial pathogens, including tuberculosis, strains resistant to all current antibiotics have arisen.

Bacterial RNA polymerase (RNAP) is a target for antibacterial therapy (Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. & Leonetti, J. (2007) *Drug Discov. Today* 12, 200-208; Ho, M., Hudson, B., Das, K., Arnold, E., Ebright, R. (2009) *Curr. Opin. Struct. Biol.* 19, 715-723; and Srivastava et al. (2011) *Curr. Opin. Microbiol.* 14, 532-543). The suitability of bacterial RNAP as a target for antibacterial therapy follows from the fact that bacterial RNAP is an essential enzyme (permitting efficacy), the fact that bacterial RNAP subunit sequences are highly conserved (permitting broad-spectrum activity), and the fact that bacterial RNAP-subunit sequences are not highly conserved in human RNAP I, RNAP II, and RNAP III (permitting therapeutic selectivity).

Accordingly, new antibacterial agents are needed.

SUMMARY OF CERTAIN EMBODIMENTS OF THE INVENTION

Certain embodiments of the present invention provide new compositions of matter that inhibit bacterial RNA polymerase and inhibit bacterial growth anticipated to have applications in analysis of RNA polymerase structure and function, control of bacterial gene expression, control of bacterial growth, antibacterial chemistry, antibacterial therapy, and drug discovery.

Accordingly, certain embodiments of the invention provide compounds according to general structural formula (I)

$$X\text{-}\alpha\text{-}Y \qquad (I)$$

wherein:
X is a moiety that binds to the salinamide binding site of a bacterial RNA polymerase;
Y is a nucleoside analog; and
α is a linker.

The invention provides methods of structure-based design, synthesis, and assay of a compound according to general structural formula (I).

The invention provides use of a compound according to general structural formula (I), e.g., to treat a bacterial infection.

The invention also encompasses crystal structures of a bacterial RNA polymerase in complex with salinamide A and a salinamide derivative.

The invention also encompasses a pharmaceutical composition comprising a compound of formula (I), or a pharmaceutically acceptable salt thereof, and a pharmaceutically acceptable carrier.

The invention also encompasses a method to inhibit a bacterial RNA polymerase comprising contacting a bacterial RNA polymerase with a compound of formula (I) as described in claim 1, or a salt thereof.

The invention also encompasses a method to treat a bacterial infection in an animal (e.g., a mammal such as a human) comprising administering a compound of formula (I) as described in claim 1, or a pharmaceutically acceptable salt thereof, to the animal.

DETAILED DESCRIPTION OF THE INVENTION

Figure 1:
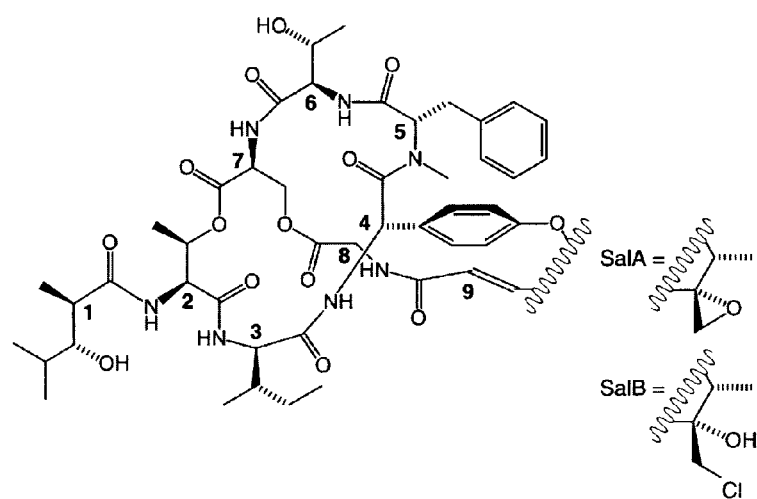
FIG. 1. Structures of SalA (compound 1) and SalB (compound 2).

The following definitions are used, unless otherwise indicated.

The term "halo" means fluoro, chloro, bromo, or iodo.

The term "alkyl" used alone or as part of a larger moiety, includes both straight and branched chains.

A combination of substituents or variables is permissible only if such a combination results in a stable or chemically feasible compound. The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents.

Unless otherwise stated, structures depicted herein are also meant to include all stereochemical forms of the structure (i.e., the R and S configurations for each asymmetric center). Therefore, single stereochemical isomers, as well as enantiomeric and diastereomeric mixtures, of the present compounds are within the scope of the invention. Similarly, E- and Z-isomers, or mixtures thereof, of olefins within the structures also are within the scope of the invention.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Unless otherwise stated, structures depicted herein also are meant to include compounds that differ only by the presence of one or more isotopically enriched atoms. For example, compounds having the present structures except for the replacement of a hydrogen atom by a deuterium or tritium, or the replacement of a carbon by a $^{13}$C- or $^{14}$C-enriched carbon, are within the scope of this invention.

Compounds of this invention may exist in tautomeric forms, such as keto-enol tautomers. The depiction of a single tautomer is understood to represent the compound in all of its tautomeric forms.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. Accordingly, certain embodiments of the invention are directed to salts of the compounds described herein, e.g., pharmaceutically acceptable salts.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The pharmaceutically acceptable salt may also be a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C$_1$-C$_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

Antibacterial Agents

Certain embodiments of the invention provide bipartite inhibitors of bacterial RNA polymerase that contain: (i) a first moiety that binds to the salinamide binding site of a bacterial RNA polymerase ("Sal target"; residues alignable to at least one of residues β675, β677, β'738, β'779, and β'782 of *Escherichia coli* RNA polymerase); (ii) a second moiety comprising a nucleoside analog; and (iii) a linker connecting said first and second moieties. An important aspect of the invention, in certain embodiments, is provision of novel inhibitors that exhibit affinities and inhibition activities higher than those of known inhibitors. An especially important aspect of the invention, in certain embodiments, is provision of novel inhibitors that inhibit bacterial RNA polymerase derivatives resistant to known inhibitors.

Accordingly, certain embodiments of the invention provide new compositions of matter that inhibit bacterial RNA polymerase and inhibit bacterial growth. The compounds are anticipated to have applications in analysis of RNA polymerase structure and function, control of bacterial gene expression, control of bacterial growth, antibacterial chemistry, antibacterial therapy, and drug discovery.

Certain embodiments of the invention provide novel bipartite compounds that, it is believed, are able to interact simultaneously with (1) the salinamide binding site of a bacterial RNA polymerase ("Sal target") and (2) the i+1 nucleoside-triphosphate binding site of the active center of a bacterial RNA polymerase ("i+1 site"). The compounds, it is believed, provide one or more of the following advantages as compared to compounds that interact with only one of the Sal target and the i+1 site: (1) higher affinity for a bacterial RNA polymerase; (2) higher potency of inhibition of a bacterial RNA polymerase; (3) higher potency of inhibition of bacterial growth; (4) higher selectivity of binding to a bacterial RNA polymerase, (6) higher selectivity of inhibition of a bacterial RNA polymerase, (7) higher selectivity of inhibition of bacterial growth; (8) ability to inhibit bacterial RNA polymerase derivatives and bacterial strains resistant to compounds that interact with only one of the Salt target and the i+1 site.

Certain embodiments of the invention provide a compound of formula (I):

$$X\text{-}\alpha\text{-}Y \quad (I)$$

wherein:

X is a moiety that binds to the salinamide binding site of a bacterial RNA polymerase;

Y is a nucleoside analog; and

α is a linker.

In certain embodiments, X is formula (I):

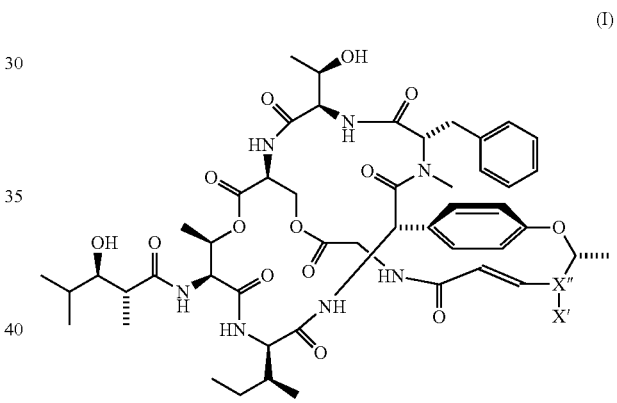

(I)

wherein:

one of X' and X" is the point of attachment of α, and the other of X' and X" is a carbon atom substituted with —OH.

In certain embodiments, X is formula (Ia):

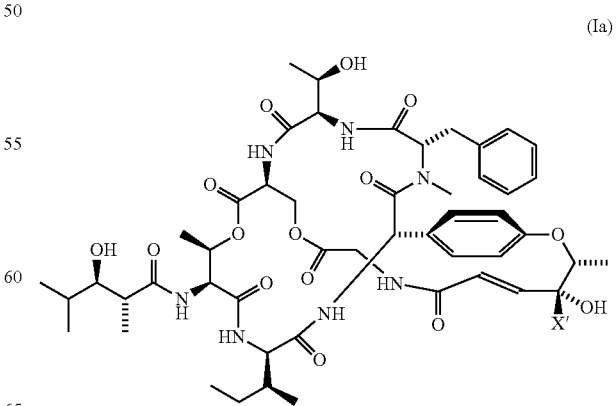

(Ia)

and wherein X' is the point of attachment of α.

In certain embodiments, X is formula (Ib):

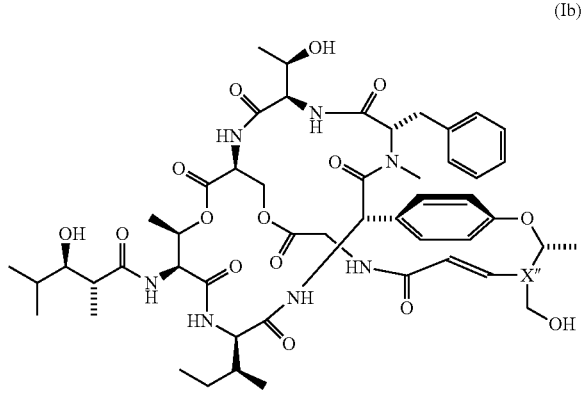

(Ib)

wherein X" is the point of attachment of α.

In certain embodiments, X is a salinamide or a salinamide derivative.

In certain embodiments, α comprises a chain of about 0 to about 20 consecutively bonded atoms.

In certain embodiments, α comprises a chain of about 0 to about 14 consecutively bonded atoms.

In certain embodiments, α comprises a chain of about 2 to about 12 consecutively bonded atoms.

In certain embodiments, α comprises a chain of about 3 to about 9 consecutively bonded atoms.

In certain embodiments, α comprises a chain of about 3 to about 5 consecutively bonded atoms.

In certain embodiments, α comprises a chain of about 0 to about 25 consecutively bonded atoms and in which the atom attached to X is one of O, S, and $NR^a$, wherein $R^a$ is H or $C_1$-$C_4$ alkyl.

In certain embodiments, α comprises a chain of about 0 to about 25 consecutively bonded atoms and in which the atom attached to Y is one of O, S, $NR^a$, and C(=O), wherein $R^a$ is H or $C_1$-$C_4$ alkyl.

In certain embodiments, α comprises a chain of about 0 to about 25 consecutively bonded atoms and in which the atoms attached to X and Y each independently are one of O, S, $NR^a$, and C(=O), wherein $R^a$ is H or $C_1$-$C_4$ alkyl.

In certain embodiments, α comprises a chain of about 0 to about 14 consecutively bonded atoms and in which the atom attached to X is one of O, S, and $NR^a$, wherein $R^a$ is H or $C_1$-$C_4$ alkyl.

In certain embodiments, α comprises a chain of about 0 to about 14 consecutively bonded atoms and in which the atom attached to Y is one of O, S, $NR^a$, and C(=O), wherein $R^a$ is H or $C_1$-$C_4$ alkyl.

In certain embodiments, α comprises a chain of about 0 to about 14 consecutively bonded atoms and in which the atoms attached to X and Y each independently are one of C(=O), O, S, and $NR^a$, wherein $R^a$ is H or $C_1$-$C_4$ alkyl.

In certain embodiments, α is a ($C_1$-$C_{25}$) alkyl, wherein one or more carbon atoms of the ($C_1$-$C_{25}$) alkyl may be optionally replaced with one or more groups independently selected from O, S, $NR^a$, and C(=O), and wherein $R^a$ is H or $C_1$-$C_4$ alkyl.

In certain embodiments, α is a ($C_1$-$C_{20}$) alkyl, wherein one or more carbon atoms of the ($C_1$-$C_{20}$) alkyl may be optionally replaced with one or more groups independently selected from O, S, $NR^a$, and C(=O), and wherein $R^a$ is H or $C_1$-$C_4$ alkyl.

In certain embodiments, α is a ($C_1$-$C_{15}$) alkyl, wherein one or more carbon atoms of the ($C_1$-$C_{15}$) alkyl may be optionally replaced with one or more groups independently selected from O, S, $NR^a$, and C(=O), and wherein $R^a$ is H or $C_1$-$C_4$ alkyl.

In certain embodiments, α is a ($C_1$-$C_{10}$) alkyl, wherein one or more carbon atoms of the ($C_1$-$C_{10}$) alkyl may be optionally replaced with one or more groups independently selected from O, S, $NR^a$, and C(=O), and wherein $R^a$ is H or $C_1$-$C_4$ alkyl.

In certain embodiments, α is a ($C_2$-$C_{20}$) alkyl, wherein one or more carbon atoms of the ($C_2$-$C_{20}$) alkyl may be optionally replaced with one or more groups independently selected from O, S, $NR^a$, and C(=O), and wherein $R^a$ is H or $C_1$-$C_4$ alkyl.

In certain embodiments, α is a ($C_2$-$C_{15}$) alkyl, wherein one or more carbon atoms of the ($C_2$-$C_{15}$) alkyl may be optionally replaced with one or more groups independently selected from O, S, $NR^a$, and C(=O), and wherein $R^a$ is H or $C_1$-$C_4$ alkyl.

In certain embodiments, α is a ($C_2$-$C_{10}$) alkyl, wherein one or more carbon atoms of the ($C_2$-$C_{10}$) alkyl may be optionally replaced with one or more groups independently selected from O, S, $NR^a$, and C(=O), and wherein $R^a$ is H or $C_1$-$C_4$ alkyl.

In certain embodiments, α is a ($C_3$-$C_{20}$) alkyl, wherein one or more carbon atoms of the ($C_3$-$C_{20}$) alkyl may be optionally replaced with one or more groups independently selected from O, S, $NR^a$, and C(=O), and wherein $R^a$ is H or $C_1$-$C_4$ alkyl.

In certain embodiments, α is a ($C_3$-$C_{15}$) alkyl, wherein one or more carbon atoms of the ($C_3$-$C_{15}$) alkyl may be optionally replaced with one or more groups independently selected from O, S, $NR^a$, and C(=O), and wherein $R^a$ is H or $C_1$-$C_1$ alkyl.

In certain embodiments, α is a ($C_3$-$C_{10}$)alkyl, wherein one or more carbon atoms of the ($C_3$-$C_{20}$)alkyl may be optionally replaced with one or more groups independently selected from O, S, $NR^a$, and C(=O), and wherein $R^a$ is H or $C_1$-$C_4$ alkyl.

In certain embodiments, α is one of —O(CH$_2$)$_n$N(R)—, —S(CH$_2$)$_n$N(R)—, and —N(R')(CH$_2$)$_n$N(R)—, wherein n is 2, 3, 4, 5, 6, 7, or 8, and R and R' each independently is one of H and $C_1$-$C_4$ alkyl.

In certain embodiments, the compound binds to a bacterial RNA polymerase.

In certain embodiments, the compound binds to a bacterial RNA polymerase with an affinity higher than the affinity of X and the affinity of Y.

In certain embodiments, the compound binds to a bacterial RNA polymerase resistant to at least one of X and Y.

In certain embodiments, the compound inhibits a bacterial RNA polymerase.

In certain embodiments, the compound inhibits a bacterial RNA polymerase with a potency higher than the potency of X and the potency of Y.

In certain embodiments, the compound inhibits a bacterial RNA polymerase resistant to at least one of X and Y.

In certain embodiments, the compound is prepared from precursors X-α' and 'α-Y, where α' and 'α are moieties that can react to form α.

In certain embodiments, the compound is prepared from precursors X-α' and 'α-Y, where α' and 'α are moieties that can react to form α, and wherein said compound is prepared from precursors X-α' and 'α-Y in the presence of a bacterial RNA polymerase.

In certain embodiments, the compound is prepared from precursors X-α' and 'α-Y, where α' and 'α are moieties that can react to form α, and wherein said compound is prepared from precursors X-α' and 'α-Y in the presence of a bacterial RNA polymerase, said bacterial RNA polymerase serving as a template for reaction of X-α' and 'α-Y.

Certain embodiments of the invention provide a method of structure-based design of a compound described herein that includes inspection of a crystal structure of a bacterial RNA polymerase in complex with one of a salinamide and a salinamide derivative.

Certain embodiments of the invention provide a method of structure-based design of a compound described herein that includes inspection of a crystal structure of a bacterial RNA polymerase in complex with one of a nucleoside, a nucleoside analog, and a nucleoside analog inhibitor of a bacterial RNA polymerase.

Certain embodiments of the invention provide a method of preparation of a compound described herein, comprising: 1) reaction of a salinamide derivative containing one of an epoxide and a halide with a compound containing one of $HO(CH_2)_nN(R)Z$, $HS(CH_2)_nN(R)Z$, and $HN(R')(CH_2)_nN(R)Z$, wherein n is 2, 3, 4, 5, 6, 7, or 8, R and R' each independently is one of H and $C_1$-$C_4$alkyl, and Z is H or a protecting group; and 2) reaction (after deprotection where Z is a protecting group) with a precursor α'-Y containing one of a carboxyl, an activated ester, and an anhydride.

Certain embodiments of the invention provide a method of preparation of a compound described herein, comprising: 1) reaction of a precursor α'-Y containing one of a carboxyl, an activated ester, and an anhydride with a compound containing one of $HN(R)(CH_2)_nOZ$, of $FIN(R)(CH_2)_nSZ$, and $HN(R')(CH_2)_nN(R)Z$, wherein n is 2, 3, 4, 5, 6, 7, or 8, R and R' each independently is one of H and $C_1$-$C_4$alkyl, and Z is H or a protecting group; and 2) reaction (after deprotection where Z is a protecting group) with a precursor α'-X containing one of an epoxide and a halide.

Certain embodiments of the invention provide an assay for inhibition of a RNA polymerase comprising contacting a bacterial RNA polymerase with a compound described herein.

Certain embodiments of the invention provide an assay for antibacterial activity comprising contacting a bacterium with a compound described herein.

Certain embodiments of the invention provide the use of a compound described herein to bind to a bacterial RNA polymerase.

Certain embodiments of the invention provide the use of a compound described herein to inhibit a bacterial RNA polymerase.

Certain embodiments of the invention provide the use of a compound described herein to inhibit bacterial gene expression.

Certain embodiments of the invention provide the use of a compound described herein to inhibit bacterial growth.

Certain embodiments of the invention provide the use of a compound described herein to treat a bacterial infection.

Certain embodiments of the invention provide the use of a compound described herein as one of a disinfectant, a sterilant, an antispoilant, an antiseptic, and an antiinfective.

Certain embodiments of the invention provide a pharmaceutical composition comprising a compound described herein and a pharmaceutically acceptable carrier.

Certain embodiments of the invention provide a compound described herein for use in therapy.

The compounds of this invention have utility as RNA polymerase inhibitors and as antibacterial agents.

Applicants have determined crystal structures of a bacterial RNA polymerase in complex with salinamide A and a salinamide derivative. The crystal structures show that the Sal target and the i+1 site are immediately adjacent to one another, show that a salinamide bound to the Sal target would be immediately adjacent to a nucleoside or nucleoside analog bound to the i+1 site, show that a salinamide bound to the Sal target could be covalently connected through a linker comprising about 0 to about 14 consecutively bonded atoms, and enable structure-based design of compounds of this invention.

Nucleoside Analogs

The term "nucleoside analog" as used herein encompasses nucleosides and analogs thereof, unphosphorylated nucleosides and analogs thereof, and singly or multiply phosphorylated nucleosides and analogs thereof.

In certain embodiments, Y is a nucleoside.

In certain embodiments, Y is a nucleoside analog.

In certain embodiments, Y is a nucleoside analog inhibitor of a bacterial RNA polymerase.

In certain embodiments, Y is a nucleoside triphosphate or a nucleoside triphosphate derivative.

In certain embodiments, Y is a nucleoside triphosphate or a nucleoside triphosphate derivative, and wherein the point of attachment of α to the nucleoside triphosphate or nucleoside triphosphate derivative is an atom of the the γ phosphate of the nucleoside triphosphate or nucleoside triphosphate derivative.

In certain embodiments, Y is a nucleoside triphosphate or a nucleoside triphosphate derivative, and wherein the point of attachment of α to the nucleoside triphosphate or nucleoside triphosphate derivative is an atom of the the β phosphate of the nucleoside triphosphate or nucleoside triphosphate derivative.

In certain embodiments, Y is a nucleoside triphosphate or a nucleoside triphosphate derivative, and wherein the point of attachment of α to the nucleoside triphosphate or nucleoside triphosphate derivative is an atom of the the α phosphate of the nucleoside triphosphate or nucleoside triphosphate derivative.

In certain embodiments, Y is a nucleoside triphosphate or a nucleoside triphosphate derivative, and wherein the point of attachment of α to the nucleoside triphosphate or nucleoside triphosphate derivative is one of the O5' atom and the C5' atom of the nucleoside triphosphate or nucleoside triphosphate derivative.

In certain embodiments, Y is a nucleoside diphosphate or a nucleoside diphosphate derivative.

In certain embodiments, Y is a nucleoside diphosphate or a nucleoside diphosphate derivative, and wherein the point of attachment of α to the nucleoside diphosphate or nucleoside diphosphate derivative is an atom of the the β phosphate of the nucleoside diphosphate or nucleoside diphosphate derivative.

In certain embodiments, Y is a nucleoside diphosphate or a nucleoside diphosphate derivative, and wherein the point of attachment of α to the nucleoside diphosphate or nucleoside diphosphate derivative is an atom of the the α phosphate of the nucleoside diphosphate or nucleoside diphosphate derivative.

In certain embodiments, Y is a nucleoside diphosphate or a nucleoside diphosphate derivative, and wherein the point of attachment of α to the nucleoside diphosphate or nucleoside diphosphate derivative is one of the O5' atom and the C5' atom of the nucleoside diphosphate or nucleoside diphosphate derivative.

In certain embodiments, Y is a nucleoside monophosphate or a nucleoside monophosphate derivative.

In certain embodiments, Y is a nucleoside monophosphate or a nucleoside monophosphate derivative, and wherein the point of attachment of α to the nucleoside monophosphate or nucleoside monophosphate derivative is an atom of the phosphate of the nucleoside monophosphate or nucleoside monophosphate derivative.

In certain embodiments, Y is a nucleoside monophosphate or a nucleoside monophosphate derivative, and wherein the point of attachment of α to the nucleoside monophosphate or nucleoside monophosphate derivative is one of the O5' atom and the C5' atom of the nucleoside monophosphate or nucleoside monophosphate derivative.

In certain embodiments, Y is a nucleoside or a nucleoside derivative.

In certain embodiments, Y is a nucleoside or a nucleoside derivative, and wherein the point of attachment of α to the nucleoside or nucleoside derivative is one of the O5' atom and the C5' atom of the nucleoside or nucleoside derivative.

In certain embodiments, Y is a ribonucleoside or a ribonucleoside derivative.

In certain embodiments, Y is a ribonucleoside or a nucleoside derivative, and wherein the point of attachment of α to the ribonucleoside or ribonucleoside derivative is one of the O5' atom and the C5' atom of the ribonucleoside or ribonucleoside derivative.

Moieties that Bind to the Salinamide Binding Site of a Bacterial RNA Polymerase

The term "moiety that binds to the salinamide binding site of a bacterial RNA polymerase" includes any compound that binds to the salinamide binding site of a bacterial RNA polymerase.

In certain embodiments, the compound binds with at least millimolar affinity

In certain embodiments, the compound binds with at least micromolar affinity

In certain embodiments the compound is a salinamide or a salinamide derivative.

In certain embodiments the compound is salinamide A (Sal; SalA; compound 1) or salinamide B (SalB; compound 2).

In certain embodiments the compound is a compound prepared in any one of Examples 7-11 herein.

Salinamides

Salinamide A (Sal; SalA; compound 1) and salinamide B (SalB; compound 2) are bicyclic depsipeptides, each consisting of seven amino-acid residues and two non-amino-acid residues (Trischman et al., *J. Am. Chem. Soc.,* 116:757-758, 1994; Moore et al., *J. Org. Chem.,* 64:1145-1150, 1999; FIG. 1). Residue 9 of SalA contains an epoxide moiety. Residue 9 of SalB contains a chlorohydrin moiety.

SalA and SalB are produced by *Streptomyces* sp. CNB-091, a marine bacterium isolated from the surface of the jellyfish *Cassiopeia xamachana* (Trischman et al., *J. Am. Chem. Soc.,* 116:757-758, 1994; Moore et al., *J. Org. Chem.,* 64:1145-1150, 1999; Moore & Seng, *Tetrahedron Lett.* 39:3915-3918, 1998). SalA also is produced by *Streptomyces* sp. NRRL 21611, a soil bacterium (Miao et al., *J. Nat. Prod.* 60, 858-861, 1997).

A total synthesis of SalA has been reported (Tan & Ma, *Angew. Chem. Int. Ed.* 47:3614-3617, 2008).

Salinamides: RNAP-Inhibitory Activity and Antibacterial Activity

It has been reported previously that SalA inhibits Gram-positive and Gram-negative bacterial RNA polymerase (RNAP) in vitro (Miao et al., *J. Nat. Prod.* 60, 858-861, 1997). It is disclosed herein that SalB also inhibits Gram-positive and Gram-negative bacterial RNAP in vitro. It further is disclosed herein that SalA and SalB do not detectably inhibit human RNAP I, II, and III.

It has been reported previously that SalA and SalB exhibit antibacterial activity against Gram-positive bacterial pathogens (Trischman et al., *J. Am. Chem. Soc.,* 116:757-758, 1994; Moore et al., *J. Org. Chem.,* 64:1145-1150, 1999). It is disclosed herein that SalA and SalB exhibit antibacterial activity against Gram-negative bacterial pathogens, including *Enterobacter cloacae, Haemophilus influenzae, Neisseria gonorrhoeae*, and *Pseudomonas aeruginosa*. It further is disclosed herein that SalA and SalB do not detectably inhibit growth of mammalian cells in culture.

The inhibition of bacterial RNAP by Sal accounts, in part or in whole, for the antibacterial activity of Sal (Ebright et al., WO/2012/129173, 2012). Sal inhibits RNA synthesis not only in vitro but also in bacterial cells in culture (Ebright et al., WO/2012/129173, 2012). Mutations in genes encoding RNAP beta and beta' subunits confer resistance to the antibacterial activity of Sal (Ebright et al., WO/2012/129173, 2012).

Salinamides: Binding Site on RNAP

The binding site on bacterial RNAP for Sal—the "Sal target" (also referred to as the "bridge-helix-cap target")—was identified by mapping sites of substitutions that confer Sal-resistance onto the three-dimensional structure of RNAP (Ebright et al., WO/2012/129173, 2012).

The binding site on bacterial RNAP for Sal was confirmed by determining crystal structures of *Escherichia coli* RNAP holoenzyme in the absence of Sal (resolution=4.0 Å) and *Escherichia coli* RNAP holoenzyme in the presence of Sal (resolution=4.2 Å) (Ebright et al., WO/2012/129173, 2012). Comparison of electron density maps revealed difference density attributable to Sal. The difference density was located in the Sal target and was in contact with or close to sites of substitutions conferring Sal resistance are obtained. The resolution was sufficient to conclude that the Sal target is the binding site on RNAP for Sal, and that sites of substitutions that confer Sal-resistance correspond to RNAP residues of RNAP that contact or are close to Sal. However, the resolution was insufficient to define the orientation of Sal relative to the Sal target and to define interatomic contacts between Sal and the Sal target.

Figure 2:
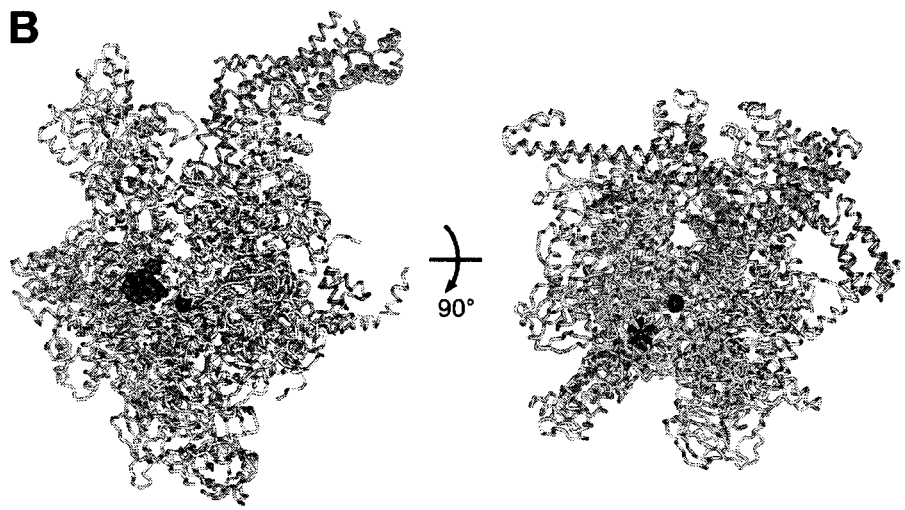
FIG. 2. Crystal structure of RNAP in complex with Sal: overview. (A) Crystallization and refinement statistics for crystal structure of *Escherichia coli* RNAP holoenzyme in complex with SalA at 3.9 Å resolution. (B) Overall structure (two orthogonal views) Gray surface labelled "*," SalA. Dark sphere, RNAP active-center $Mg^{2+}$ ion. (C) Electron density and model for SalA (two orthogonal views). Mesh, $F_o\text{-}F_c$ omit map for SalA (NCS averaged and contoured at 3.2σ). BH, bridge helix. FL, fork loop. LR, link region.
Figure 2:
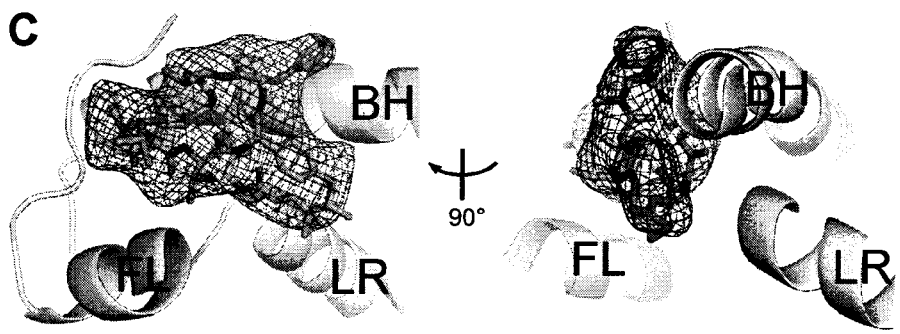
Figure 3:
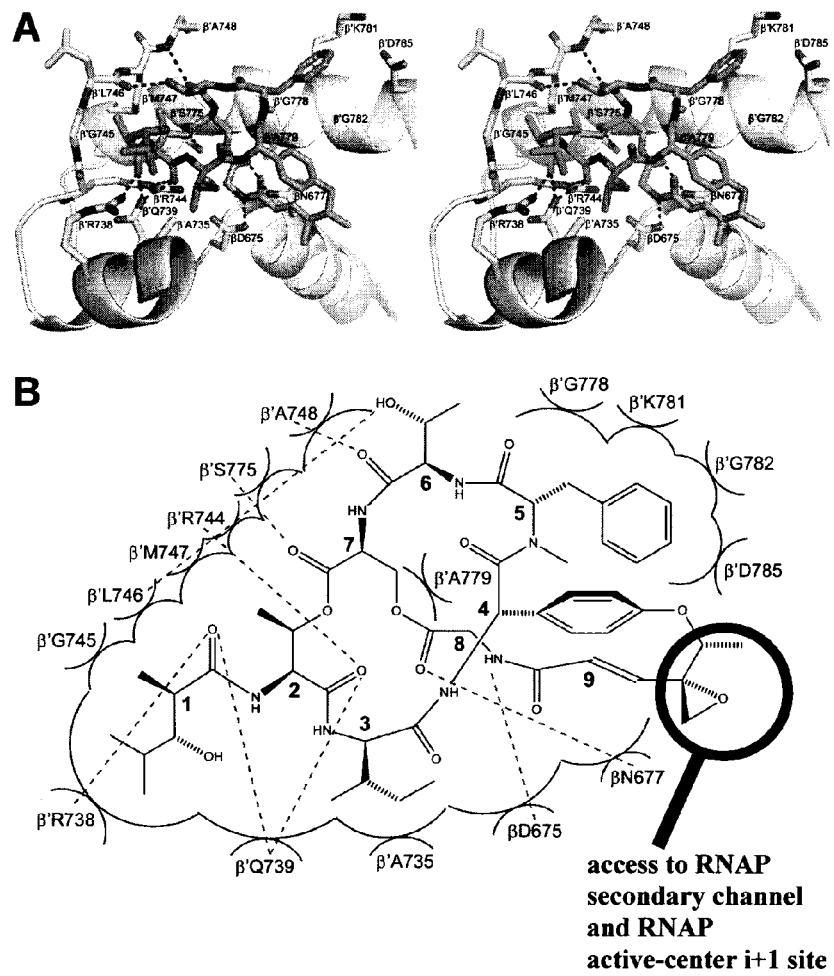
FIG. 3. Crystal structure of RNAP in complex with Sal: details. (A) Stereoview showing RNAP-Sal interactions as observed in the crystal structure of *Escherichia coli* RNAP holoenzyme in complex with SalA at 3.9 Å resolution. Gray, RNAP backbone (ribbon representation) and RNAP sidechains (stick representation). Dashed lines, H-bonds. (B) Schematic summary of contacts between RNAP and SalA. Black circle, part of SalA that has unobstructed access to RNAP secondary channel and RNAP active-center i+1 site. Dashed lines, H-bonds. Arcs, van der Waals interactions.

Disclosed herein are crystal structures of *Escherichia coli* RNAP holoenzyme in the absence of Sal and *Escherichia coli* RNAP holoenzyme in the presence of Sal at a resolution sufficient to define the orientation of Sal relative to the Sal target and to define interatomic contacts between Sal and the Sal target (resolution=3.9 Å; FIGS. 2-3).

Figure 4:
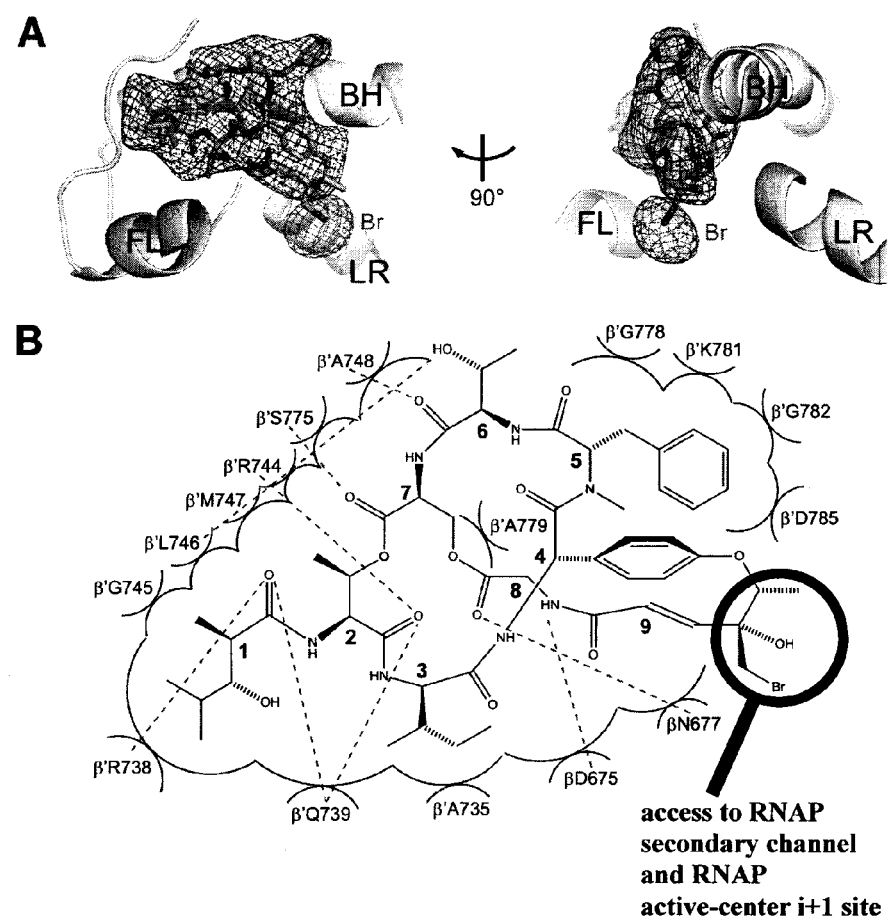
FIG. 4. Crystal structure of RNAP in complex with Sal derivative. (A) Electron density, bromine anomalous difference density, and model for *Escherichia coli* RNAP holoenzyme in complex with Sal-Br (two orthogonal views). Dark mesh, $F_o$-$F_c$ omit map for SalA (NCS averaged and contoured at 3.2σ). Light mesh labelled "Br", bromine anomalous difference density (contoured at 7σ). BH, bridge helix. FL, fork loop. LR, link region. (B) Schematic summary of contacts between RNAP and Sal-Br. Dashed lines, H-bonds. Black circle, part of SalA that has unobstructed access to RNAP secondary channel and RNAP active-center i+1 site. Arcs, van der Waals interactions.

Further disclosed herein are electron density and bromine anomalous difference density for *Escherichia coli* RNAP holoenzyme in complex with Sal-Br (FIG. 4). The location of the Sal-Br bromine anomalous difference density peak relative to the Sal target unequivocally confirms the orientation of Sal relative to the Sal target (FIG. 4).

The Sal target is located adjacent to, and partly overlaps, the RNAP polymerase active center (Ebright et al., WO/2012/129173, 2012). It is inferred that Sal most likely inhibits RNAP by inhibiting RNAP active-center function.

The Sal target does not overlap the RNAP active-center $Mg^{2+}$ ion and does not overlap RNAP residues that interact with the DNA template, the RNA product, or the nucleoside triphosphate substrate (Ebright et al., WO/2012/129173, 2012). It is inferred Sal inhibits RNAP active-center function allosterically, through effects on RNAP conformation, rather than through direct interactions with RNAP residues that mediate bond formation, product binding, and substrate binding.

The Sal target overlaps an RNAP active-center module referred to as the "bridge-helix cap," which, in turn, comprises three active-center subregions: the "bridge-helix N-terminal hinge" (BH-H$_N$), the "F-loop," and the "link region" (Ebright et al., WO/2012/129173, 2012). It has been proposed that the BH-H$_N$ undergoes hinge-opening/hinge-closing conformational changes coupled to, and essential for, the nucleotide-addition cycle in RNA synthesis, and that the F-loop and link region, coordinate these conformational changes (Weinzierl, BMC Biol. 8:134, 2010; Hein & Landick, BMC Biol. 8:141, 2010; Kireeva et al., BMC Biophys. 5:11-18, 2012; Nedialkov et al., Biochim. Biophys. Acta 1829:187-198, 2013). It is inferred that Sal may inhibit RNAP active-center function by inhibiting BH-H$_N$ hinge-opening and/or hinge-closing (Ebright et al., WO/2012/129173, 2012).

The Sal target is located near to, but does not overlap, the target of the rifamycin antibacterial agents (e.g., rifampin, rifapentine, rifabutin, and rifalazil), which are RNAP inhibitors in current clinical use in antibacterial therapy (Ebright et al., WO/2012/129173, 2012; see Darst. Trends Biochem. Sci 29:159-162, 2004; Chopra, Curr. Opin. Investig. Drugs 8:600-607, 2007; Villain-Guillot et al., Drug Discov. Today 12:200-208, 2007; Ho et al., Curr. Opin. Struct. Biol. 19:715-723, 2009). Consistent with the lack of overlap between the Sal target and the rifamycin target, Sal-resistant mutants are not cross-resistant to rifamycins, and rifamycin-resistant mutants are not cross-resistant to Sal (Ebright et al., WO/2012/129173, 2012).

The Sal target also is located near to, but does not overlap, the target of CBR703, an RNAP inhibitor under investigation for clinical use in antibacterial therapy (Ebright et al., WO/2012/129173, 2012; see Darst. Trends Biochem. Sci. 29:159-162, 2004; Chopra, Curr. Opin. Investig. Drugs 8:600-607, 2007; Villain-Guillot et al., Drug Discov. Today 12:200-208, 2007). Consistent with the lack of overlap between the Sal target and the CBR703 target, Sal-resistant mutants are not cross-resistant to CBR703, and CBR703-resistant mutants are not cross-resistant to Sal (Ebright et al., WO/2012/129173, 2012).

It is disclosed herein that the Sal target does not overlap the targets of the RNAP inhibitors streptolydigin, myxopyronin, and lipiarmycin (see Chopra, Curr. Opin. Investig. Drugs 8:600-607, 2007; Villain-Guillot et al., Drug Discov. Today 12:200-208, 2007; Ho et al., Curr. Opin. Struct. Biol. 19:715-723, 2009; Srivastava et al., Curr. Opin. Microbiol. 14:532-543, 2011). The Sal target is located adjacent to, but does not overlap, and the streptolydigin target. The Sal target is distant from the myxopyronin target and the lipiarmycin target. It further is disclosed herein that, consistent with the absence of overlap of targets and mechanisms, Sal-resistant mutants do not exhibit cross-resistance with streptolydigin, myxopyronin, and lipiarmycin, and, conversely, streptolydigin-resistant, myxopyronin-resistant, and lipiarmycin-resistant mutants do not exhibit cross-resistance with Sal.

Salinamides: Mechanism of Inhibition of RNAP

It is disclosed herein that Sal inhibits RNAP through a mechanism that is different from the mechanisms of rifamycins, streptolydigin, myxopyronin, and lipiarmycin.

It is disclosed herein that Sal does not inhibit formation of the RNAP-promoter open complex in transcription initiation. This result indicates that Sal inhibits RNAP through a mechanism different from the mechanisms of myxopyronin and lipiarmycin (which inhibit formation of RNAP-promoter open complex).

It is disclosed herein that Sal inhibits nucleotide addition in both transcription initiation and transcription elongation. Sal inhibits both primer-dependent transcription initiation and de novo transcription initiation. In primer-dependent transcription initiation, Sal inhibits all nucleotide-addition steps, including the first nucleotide-addition step yielding a 3-nucleotide RNA product from a 2-nucleotide RNA primer and an NTP. In de novo transcription initiation, Sal inhibits all nucleotide-addition steps, including the first nucleotide-addition step yielding a 2-nucleotide RNA product from two NTPs. These results confirm that Sal inhibits RNAP through a mechanism different from the mechanisms of myxopyronin and lipiarmycin (which do not inhibit transcription elongation) and indicate that Sal inhibits RNAP through a mechanism different from the mechanism of rifamycins (which do not inhibit the first nucleotide addition step in transcription initiation and which do not inhibit transcription elongation).

It is disclosed herein that transcription inhibition by Sal does not require the RNAP active-center subregion referred to as the trigger loop. Sal inhibits wild-type RNAP and an RNAP-derivative having a deletion of the trigger loop to equal extents and with nearly equal concentration-dependences. This result indicates that Sal inhibits RNAP through a mechanism different from the mechanisms of streptolydigin (for which transcription inhibition requires the trigger loop).

It is disclosed herein that transcription inhibition by Sal is noncompetitive with respect to NTP substrate. It is inferred that Sal does not inhibit the NTP binding sub-reaction of the nucleotide-addition cycle, but, instead, inhibits one or more of the bond-formation, pyrophosphate-release, and translocation sub-reactions of the nucleotide-addition cycle.

Salinamides: Novel Sal Analogs

The syntheses disclosed herein of Sal-Br, Sal-OH, Sal-OR, Sal-SR, and Sal-NHR show that the SalA epoxide moiety and SalB chlorohydrin moieties provide chemical reactivity that can be exploited for semi-synthesis of novel Sal analogs (Examples 7-11). The observation that certain synthesized Sal analogs retain RNAP-inhibitory activity and antibacterial activity shows that certain substitutions of the SalA epoxide moiety and SalB chlorohydrin moiety can be tolerated without loss of activity (Tables 1-2). The crystal structure of RNAP-Sal indicates that the SalA epoxide moiety and SalB chlorohydrin moiety make few or no interactions with RNAP and are located at the entrance to the Sal binding pocket, directed towards the RNAP active-center i+1 site (FIGS. 3-4).

These findings set the stage for structure-based design of semi-synthetic, novel Sal analogs with increased potency.

For example, equipping Sal, through the SalA epoxide or SalB chlorohydrin, with a moiety able to interact with the RNAP active-center i+1 site may provide additional energetically favorable interactions with RNAP. A bipartite compound comprising Sal linked to a nucleoside, a nucleoside analog, or a nucleoside analog inhibitor may be able to interact simultaneously with the Sal target and the RNAP active-center i+1 site, and therefore, may be able to exhibit very high biding affinities and very high potencies of inhibition.

Conversely, equipping a nucleoside, a nucleoside analog, or a nucleoside analog RNAP inhibitor with a moiety able to interact with the Sal target may provide additional energetically favorable interactions with RNAP and may provide a means increasing affinity, increasing potency; and increasing bacterial-vs.-human selectivity.

RNAP Active-Center i+1 Site

The RNAP active-center contains two nucleoside/nucleotide binding sites—the "i site" and the "i+1 site" (also referred to as the "P site" and "A site")—flanking a catalytic Mg$^{2+}$ ion (Zhang & Landick, Substrate loading, nucleotide addition, and translocation by RNA polymerase. In RNA Polymerase as Molecular Motors, Buc and Strick, Eds., Royal Society, Cambridge, pp. 206-229, 2009).

The RNAP active-center i+1 site serves as the binding site for the second initiating nucleoside triphosphate in de novo transcription initiation (Zhang & Landick, Substrate loading, nucleotide addition, and translocation by RNA polymerase. In *RNA Polymerase as Molecular Motors*, Buc and Strick, Eds., Royal Society, Cambridge, pp. 206-229, 2009).

The RNAP active-center i+1 site also serves as the binding site for the extending nucleoside triphosphate in primer-dependent transcription initiation and transcription elongation (Zhang & Landick, Substrate loading, nucleotide addition, and translocation by RNA polymerase. In *RNA Polymerase as Molecular Motors*, Buc and Strick, Eds., Royal Society, Cambridge, pp. 206-229, 2009).

The RNAP active-center i+1 site also is the binding site for nucleoside analog inhibitors of RNAP (http://projectreporter.nih.gov/project_info_description.cfm?aid=8474439& icde=15257240&ddparam=&ddvalue=&ddsub=&cr=2& csb=default&cs=ASC).

The RNAP active-center i+1 site is located adjacent to the Sal target but does not overlap the Sal target (FIGS. 3-4).

A nucleoside triphosphate can bind to the i+1 site in a "pre-insertion mode" (Vassylyev et al., *Nature* 448:163-168, 2007; Zhang & Landick, Substrate loading, nucleotide addition, and translocation by RNA polymerase. In *RNA Polymerase as Molecular Motors*, Buc and Strick, Eds., Royal Society, Cambridge, pp. 206-229, 2009; Martinez-Rubico & Cramer, *Biochim. Biophys Acta,* 1829:9-19, 2013). In this binding mode, the base moiety of the nucleoside triphosphate base-pairs with the base of the DNA template-strand nucleotide in the i+1 site and stacks on the base of the RNA nucleotide in the i site, but the sugar and triphosphate moieties are not properly oriented for catalysis, the active-center is not dehydrated, and the RNAP active-center trigger loop is not closed.

A nucleoside triphosphate also can bind to the i+1 site in an "insertion mode" (Vassylyev et al., *Nature* 448:163-168, 2007; Zhang & Landick, Substrate loading, nucleotide addition, and translocation by RNA polymerase. In *RNA Polymerase as Molecular Motors*, Buc and Strick, Eds., Royal Society, Cambridge, pp. 206-229, 2009; Martinez-Rubico & Cramer, *Biochim. Biophys Acta,* 1829:9-19, 2013). In this binding mode, the base moiety of the nucleoside triphosphate base-pairs with the base of the DNA template-strand nucleotide in the i+1 site and stacks on the base of the RNA nucleotide in the i site, the sugar and triphosphate moieties are properly oriented for catalysis, the active-center is dehydrated, and the RNAP active-center trigger loop is closed.

It is thought that both the nucleoside triphosphate pre-insertion-mode complex and the nucleoside triphosphate pre-insertion-mode complex are functionally important states (Vassylyev et al., *Nature* 448:163-168, 2007; Zhang & Landick, Substrate loading, nucleotide addition, and translocation by RNA polymerase. In *RNA Polymerase as Molecular Motors*, Buc and Strick, Eds., Royal Society, Cambridge, pp. 206-229, 2009; Martinez-Rubico & Cramer, *Biochim. Biophys Acta,* 1829:9-19, 2013). Specifically, it is thought that nucleoside triphosphate binding is a multistep process, in which a nucleoside triphosphate interacts with the RNAP active-center i+1 site first in a pre-insertion mode and then in an insertion mode.

In principle, isomerization of a pre-insertion-mode complex to an insertion-mode complex, may be a concerted, single-step reaction, in which re-orientation of the sugar and triphosphate moieties, dehydration of the active center, and closure of the trigger loop occur simultaneously.

Alternatively, in principle, isomerization of a pre-insertion-mode complex to an insertion-mode complex, may be a non-concerted, multi-step reaction, in which, for example, at least one of re-orientation of the sugar and triphosphate moieties and dehydration of the active center may precede closure of the trigger loop.

Accordingly, there may exist not only an initial pre-insertion-mode state and final insertion-mode state, but also one or more intermediate states.

Figure 5:
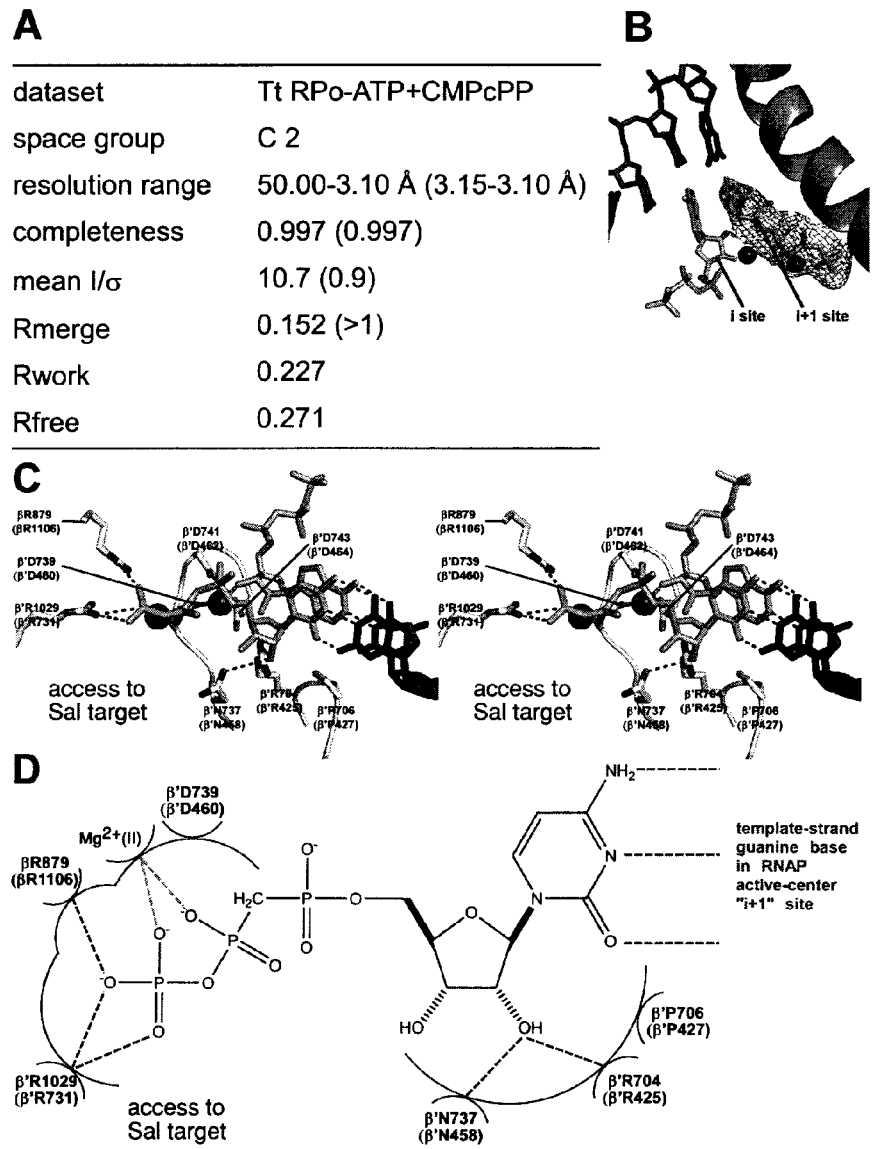
FIG. 5. Crystal structure of transcription initiation complex containing nucleoside triphosphate analog in RNAP active-center i+1 site: pre-insertion binding mode. (A) Crystallization and refinement statistics for crystal structure of *Thermus thermophilus* RPo-ATP-CMPcPP at 3.1 Å resolution. (B) Electron density and model. Mesh, $F_o$-$F_c$ omit map for CMPcPP:$Mg^{2+}$(II). Gray ribbon, RNAP bridge helix. Gray sticks, ATP (left) and CMPcPP (right). Dark gray sticks, DNA template strand. Dark gray spheres, $Mg^{2+}$(I) (left) and $Mg^{2+}$(II) (right). (C) Stereoview. Gray sticks, ATP (back) and CMPcPP (front). Light gray, RNAP backbone (ribbons) and RNAP sidechains (sticks). Dark gray spheres, $Mg^{2+}$(I) (right) and $Mg^{2+}$(II) (left). Dashed lines, H-bonds. Other features as in B. (D) Schematic summary of contacts between RNAP and pre-insertion-mode CMPcPP. Dashed lines, H-bonds. Arcs, van der Waals interactions.

Disclosed herein is a crystal structure of *Thermus thermophilus* transcription initiation complex containing a nucleoside triphosphate analog bound to the RNAP active-center i+1 site in a pre-insertion mode (resolution=3.1 Å; FIG. 5).

Figure 6:
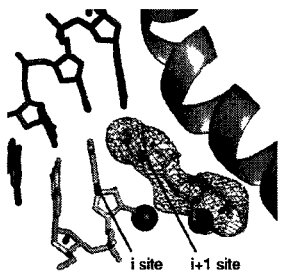
FIG. 6. Crystal structure of transcription initiation complex containing nucleoside triphosphate analog in RNAP active-center i+1 site: insertion binding mode. (A) Crystallization and refinement statistics for crystal structure of *Thermus thermophilus* RPo-GpA-CMPcPP at 3.1 Å resolution. (B) Electron density and model. Mesh, $F_o$-$F_c$ omit map for CMPcPP:$Mg^{2+}$(II). Gray ribbon, RNAP bridge helix. Gray sticks, GpA (left) and CMPcPP (right). Dark gray sticks, DNA template strand. Dark gray spheres, $Mg^{2+}$(I) (left) and $Mg^{2+}$(II) (right). (C) Stereoview. Light gray, RNAP backbone (ribbons) and RNAP sidechains (sticks). Dashed lines, H-bonds. Other features as in B. (D) Schematic summary of contacts between RNAP and insertion-mode CMPcPP. Dashed lines, H-bonds. Arcs, van der Waals interactions.
Figure 6:
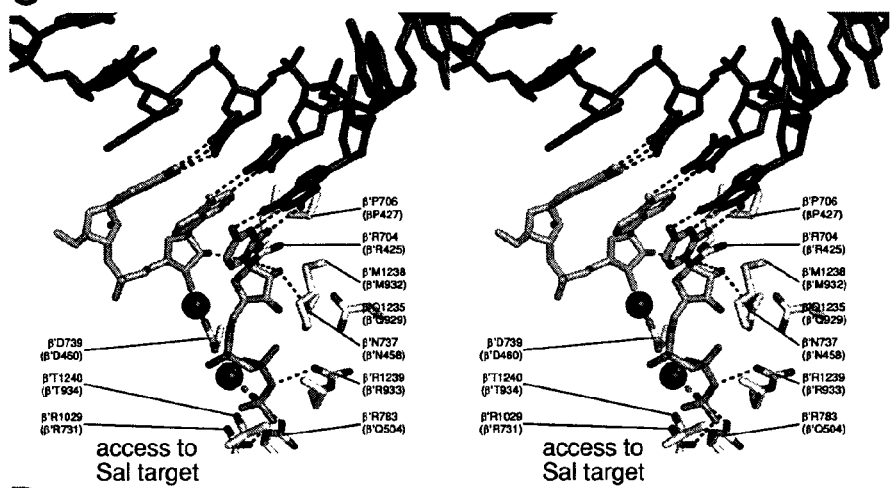
Figure 6:
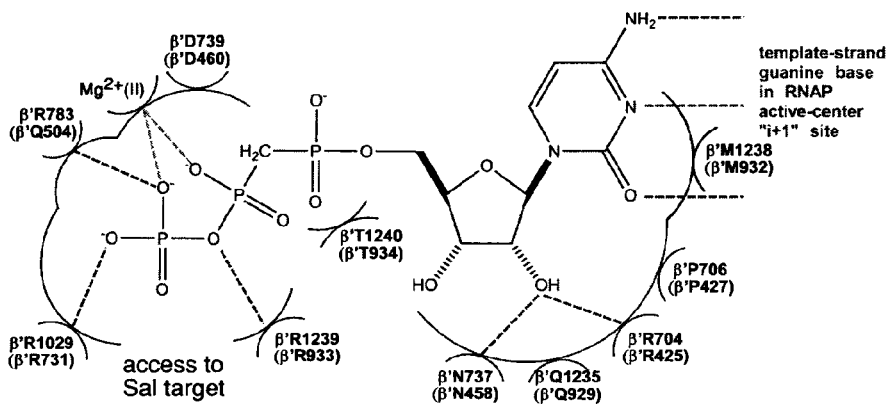

Also disclosed herein is a crystal structure of *Thermus thermophilus* transcription initiation complex containing a nucleoside triphosphate analog bound to the RNAP active-center i+1 site in an insertion mode (resolution=3.1 Å; FIG. 6).

Bipartite Inhibitors: Sal Target and the RNAP Active-Center i+1 Site

The invention provides novel bipartite compounds that, it is believed, are able to interact simultaneously with (1) the RNAP Sal target and (2) the RNAP active-center i+1 site of the active center. The compounds, it is believed, provide one or more of the following advantages as compared to compounds that interact with only one of the Sal target and the i+1 site: (1) higher affinity for a bacterial RNAP; (2) higher potency of inhibition of a bacterial RNAP; (3) higher potency of inhibition of bacterial growth; (4) higher selectivity of binding to a bacterial RNAP, (6) higher selectivity of inhibition of a bacterial RNAP, (7) higher selectivity of inhibition of bacterial growth; and (8) ability to inhibit bacterial RNAP derivatives and bacterial strains resistant to compounds that interact with only one of the Salt target and the i+1 site.

The invention provides compounds that contain: (1) a first moiety that binds to the RNAP Sal target; (2) a second moiety that contains a nucleoside, a nucleoside analog, or a nucleoside analog inhibitor that binds to the RNAP active-center i+1 site; and (3) a linker connecting said first and second moieties, The invention also provides examples of appropriate first moieties and functionalizable atoms thereof: SalA (functionalizable through residue-9 epoxide carbon) and SalB (functionalizable through residue-9 chlorohydrin carbon atom).

One embodiment employs as first moiety a salinamide or a salinamide derivative.

Another embodiment employs as first moiety an entity that binds to the RNAP Sal target but that is not a salinamide or a salinamide derivative.

The invention also provides examples of appropriate second moieties and functionalizable atoms thereof: a nucleoside triphosphate (functionalizable through an atom of the γ phosphate, an atom of the β phosphate, an atom of the α phosphate, O5', or C5'); a nucleoside diphosphate (functionalizable through an atom of the β phosphate, an atom of the α phosphate, O5', or C5'); a nucleoside monophosphate (functionalizable through an atom of the phosphate, O5', or C5'); and a nucleoside (functionalizable through O5' or C5').

One embodiment employs as second moiety a nucleoside.

Another embodiment employs as second moiety a nucleoside analog.

Another embodiment employs as second moiety a nucleoside analog RNAP inhibitor

Another embodiment employs as second moiety a non-selective nucleoside analog RNAP inhibitor (a nucleoside analog inhibitor that exhibits comparable RNAP-inhibitory activities against a bacterial RNAP and a human RNAP).

Another embodiment employs as second moiety a selective nucleoside analog RNAP inhibitor (a nucleoside analog inhibitor that exhibits comparable RNAP-inhibitory activities against a bacterial RNAP and a human RNAP).

The invention also provides a method to design said compounds, comprising: (1) using molecular modelling software to superimpose a crystal structure of RNAP in complex with a first moiety that binds to the Sal target and a crystal structure of RNAP in complex with a second moiety containing nucleoside, a nucleoside analog, or a nucleoside analog inhibitor that binds to the RNAP active-center i+1 site; (2) using molecular modelling software to identify a linker measure the distance between a functionalizable atom of the first moiety and a functionalizable atom of the second moiety in the superimposed structures; (3) selecting a linker having length and character appropriate to link the functionalizable atom of the first moiety to the functionalizable atom of the second moiety (e.g., a linker comprising a chain of at least R-2 consecutive bonds and no more than 2(R-2) consecutive bonds, where R is the distance in A).

The invention also provides crystal structures useful for design of said compounds (FIGS. 2-6).

Figure 7:
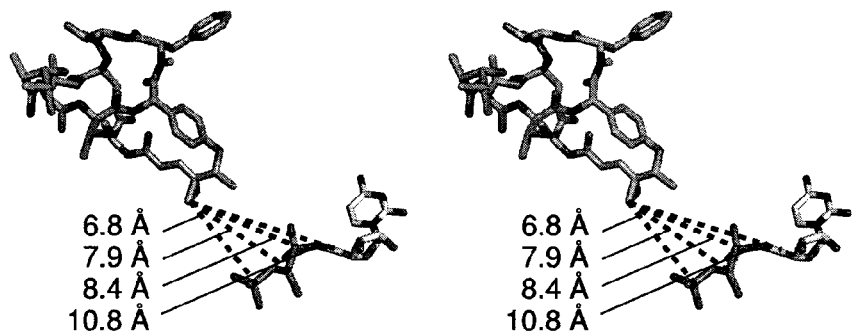
FIG. 7. Structural model of Sal bound to Sal target and nucleoside triphosphate analog bound to RNAP active-center i+1 site: pre-insertion mode. Stereoview of SalA (left) and pre-insertion mode nucleoside triphosphate analog. Dashed lines connect the SalA residue-9 epoxide moiety to the nucleoside triphosphate analog Pγ, Pβ, Pα, and C5' atoms (left to right). Numbers are distances between the SalA residue-9 epoxide moiety and the NTP analog Pγ, Pβ, Pα, and C5' atoms (top to bottom).
Figure 8:
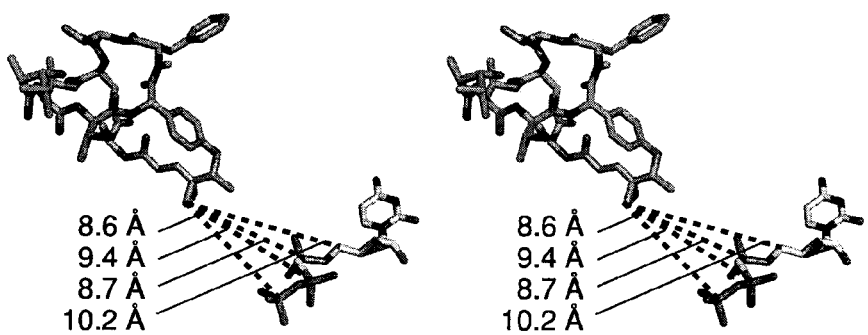
FIG. 8. Structural model of Sal bound to Sal target and nucleoside triphosphate analog bound to RNAP active-center i+1 site: insertion mode. Stereoview of SalA (left) and insertion mode nucleoside triphosphate analog. Dashed lines connect the SalA residue-9 epoxide moiety to the nucleoside triphosphate analog Pγ, Pβ, Pα, and C5' atoms (left to right). Numbers are distances between the SalA residue-9 epoxide moiety and the NTP analog Pγ, Pβ, Pα, and C5' atoms (top to bottom).

The invention also provides structural models useful for design of said compounds (FIGS. 7-8).

Disclosed herein is a structural model that defines the spatial relationship between Sal bound to the Sal target and a nucleoside triphosphate analog bound to the RNAP active-center i+1 site in a pre-insertion mode (obtained by superimposing a crystal structure of RNAP-Sal and a crystal structure of a transcription initiation complex containing a nucleoside triphosphate analog in a pre-insertion mode; FIG. 7).

Disclosed herein is a structural model that defines the spatial relationship between Sal bound to the Sal target and a nucleoside triphosphate analog bound to the RNAP active-center i+1 site in an insertion mode (obtained by superimposing a crystal structure of RNAP-Sal and a crystal structure of a transcription initiation complex containing a nucleoside triphosphate analog in an insertion mode; FIG. 8).

The invention also provides methods to prepare said compounds.

The invention also provides synthetic intermediates useful for prepartion of said compounds.

Administration of Pharmaceutical Compositions

The compounds described herein may be formulated as pharmaceutical compositions and administered to a mammalian host, such as a human male or female patient in a variety of forms adapted to the chosen route of administration (e.g., orally or parenterally, by intravenous, intramuscular, topical or subcutaneous routes).

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 150 mg/kg, e.g., from about 10 to about 125 mg/kg of body weight per day, such as 3 to about 75 mg per kilogram body weight of the recipient per day, preferably in the range of 6 to 120 mg/kg/day, most preferably in the range of 15 to 90 mg/kg/day.

The compound may be conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

EXAMPLES

Example 1

Crystal Structure of RNAP in Complex with Sal

Crystal structures of *Escherichia coli* RNAP holoenzyme at 3.9 Å resolution and *Escherichia coli* RNAP holoenzyme in complex with SalA at 3.9 Å resolution were determined as follows:

Crystallization trials were performed using Crystal Former microfluidic chips (Microlytic, Inc.) and SmartScreen solutions (Microlytic, Inc.) (precipitant inlet: 1.5 µl screening solution; sample inlet: 1.5 µl 10 mg/ml *Escherichia coli* RNAP holoenzyme in 10 mM Tris-HCl, pH 7.9, 100 mM NaCl, 1% glycerol; 22° C.). Under one condition, small crystals appeared within two days. Conditions were optimized using the hanging-drop vapor-diffusion technique at 22° C. The optimized conditions (reservoir: 500 µl 0.1 M HEPES, pH 7.0, 0.2 M $CaCl_2$, and 18% PEG400; drop: 1 µl 10 mg/ml *Escherichia coli* RNAP holoenzyme in 10 mM Tris-HCl, pH 7.9, 100 mM NaCl, 1% glycerol plus 1 µl reservoir solution; 22° C.) yielded large crystals with dimensions of 0.2 mm×0.2 mm x 0.2 mm in one week. SalA was soaked into RNAP crystals, yielding RNAP-Sal crystals, by addition of 0.2 µl 20 mM SalA or Sal-Br in (±)-2-methyl-2,4-pentanediol (Hampton Research, Inc.) to the crystallization drop and incubation 30 min at 22° C. RNAP and RNAP-SalA crystals were transferred to reservoir solutions containing 15% (v/v) (2R,3R)-(−)-2,3-butanediol (Aldrich, Inc.) and then flash-cooled with liquid nitrogen.

Diffraction data were collected from cryo-cooled crystals at Cornell High Energy Synchrotron Source beamline F1 and at Brookhaven National Laboratory beamline X25. Data were processed using HKL2000.

The structure of *Escherichia coli* RNAP holoenzyme was solved by molecular replacement using AutoMR. The search model was generated by starting with the crystal structure of *Thermus thermophilus* RNAP-promoter open complex (PDB 4G7H), deleting DNA and non-conserved protein domains, modelling *Escherichia coli* RNAP holoenzyme $\alpha^I$ and $\alpha^{II}$ subunit N-terminal domains by superimposing the crystal structure of *Escherichia coli* RNAP holoenzyme α N-terminal domain dimer (PRB 1BDF), and modelling *Escherichia coli* RNAP holoenzyme β,β', ω, and $\sigma^{70}$ subunits using Sculptor (backbone and sidechain atoms for identical residues; backbone and Cβ atoms for non-identical residues). Two RNAP molecules were present in the asymmetric unit. Crystal structures of *Escherichia coli* RNAP holoenzyme α subunit C-terminal domain (PDB 3K4G), the *Escherichia coli* RNAP holoenzyme β subunit β2-βi4 and βflap-βi9 domains (PDB 3LTI and PDB 3LUO), and *Escherichia coli* RNAP holoenzyme $\sigma^{70}$ region 2 (PDB 1 SIG) were fitted manually to the (Fo-Fc) difference electron density map. Early-stage refinement of the structure was performed using Phenix and included rigid-body refinement of each RNAP molecule in the asymmetric unit, followed by rigid-body refinement of each subunit of each RNAP molecule, followed by rigid-body refinement of 216 segments of each RNAP molecule, followed by group B-factor refinement with one B-factor group per residue, using Phenix. Density modification, including non-crystallographic-symmetry averaging and solvent flattening, were performed to remove model bias and to improve phases. The resulting maps allowed segments that were not present in the search model to be built manually using Coot. Cycles of iterative model building with Coot and refinement with Phenix improved the model. The final *E. coli* RNAP holoenzyme model, refined to Rwork and Rfree of 0.276 and 0.325, respectively, was deposited in the PDB with accession code 4MEY.

The structure of *Escherichia coli* RNAP holoenzyme coli in complex with SalA was solved by molecular replacement in AutoMR, using the above crystal structure of *Escherichia coli* RNAP holoenzyme as the search model. After rigid-body refinement with 216 domains, an electron density feature corresponding to one molecule of SalA per holoenzyme was clearly visible in the (Fo-Fc) difference map. A structural model of SalA derived from the crystal structure of SalB (CSD 50962; enantiomorph corrected based on Moore et al., et al., *J. Org. Chem.*, 64:1145-1150, 1999) was fitted to the (Fo-Fc) difference map with minor adjustments of SalA conformation. The final *Escherichia coli* RNAP holoenzyme-SalA complex model, refined to Rwork and Rfree of 0.286 and 0.325, respectively, was deposited in the PDB with accession code 4MEX. The structure of *E. coli* RNAP holoenzyme in complex with Sal at 3.9 Å resolution shows unambiguous experimental electron density for Sal in the genetically-defined Sal target, confirming the hypothesis that the Sal target represents the Sal binding site on RNAP (FIG. 2).

The structure shows that Sal binds within the RNAP bridge-helix cap, making direct interactions with the BH-H$_N$, the fork loop, and the link region (FIGS. 2-3).

Sal makes direct interactions with all residues at which substitutions conferring highest-level (≥128-fold) Sal-resistance are obtained (β' residues R738, A779, and G782, and β residues D675 and N677; FIG. 3).

Six residues that make direct contact with SalA are conserved across Gram-positive bacterial RNAP, Gram-negative bacterial RNAP, and human RNAP. Eight residues that contact Sal are conserved in Gram-positive bacterial RNAP and Gram-negative bacterial RNAP, but are not conserved, and indeed are radically different, in human RNAP. The observed interactions account for and explain the observation that Sal inhibits Gram-positive and Gram-negative bacterial RNAP, but does not inhibit human RNAP.

Sal binds within a ~600 Å$^3$ pocket formed by the BH-H$_N$, the fork loop, and the link region. Backbone atoms of residues that form the pocket have the same conformations in RNAP holoenzyme in the absence of Sal and in RNAP holoenzyme in complex with Sal, indicating that the pocket pre-exists in RNAP holoenzyme in the absence of Sal.

The pocket opens at one end onto the RNAP secondary channel and the RNAP active-center "i+1" NTP-insertion site. It seems likely that Sal enters the pocket from the RNAP secondary channel or the active-center "i+1" site.

Within the binding pocket, Sal residues 4, 5, 7, and 8 interact with the RNAP BH-H$_N$, Sal residues 1-3 and 6-7 interact with the RNAP fork loop, and Sal residues 8 and 9 interact with the RNAP link region (FIG. 3). Sal residue 9 is at the end of the pocket that opens onto the RNAP secondary channel and the active-center "i+1" site (FIG. 3). The Sal residue-9 epoxide moiety and methyl moiety extend into this opening and make only limited interactions with residues of RNAP (FIG. 3).

The crystal structure of the RNAP-Sal complex also defines effects of Sal on RNAP conformation.

The crystal structure of RNAP-Sal shows that Sal interacts with the BH-H$_N$ in an "open" (unbent) state. This conformation is different from the "closed" (bent) BH-H$_N$ conformation that has been observed in molecular-dynamics simulations of nucleotide-addition reactions in transcription elongation complexes, and that has been postulated to serve as an intermediate in the pyrophosphate-release and/or translocation reactions of the nucleotide-addition cycle (Weinzierl, *BMC Biol.* 8:134, 2010; Hein & Landick, *BMC Biol.* 8:141, 2010; Kireeva et al., *BMC Biophys.* 5:11-18, 2012; Nedialkov et al., *Biochim. Biophys. Acta* 1829:187-198, 2013). It is inferred that Sal interacts with an "open" (unbent) BH-H$_N$ conformational state, and it is hypothesized that, through its interactions with that state, Sal stabilizes that state and inhibits BH-H$_N$ conformational dynamics required for nucleotide addition.

In the crystal structure of RNAP-Sal, the RNAP active-center trigger loop is disordered. Modeling indicates that the structure of RNAP-Sal could accommodate the "open" (unfolded) trigger loop conformations observed in crystal structures of some transcription initiation and elongation complexes, but could not accommodate the "closed" (folded) trigger loop conformations observed in other crystal structure of transcription initiation and elongation complexes. It is inferred that Sal favors "open" (unfolded) trigger loop conformational states, and may disfavor the "closed" (folded) trigger loop conformational states. However, experiments with an RNAP derivative lacking the trigger loop indicate that the trigger loop is not essential for transcription inhibition by Sal. Therefore, although effects of Sal on trigger loop conformation could contribute to transcription inhibition by Sal, they are neither necessary nor sufficient for transcription inhibition by Sal.

The interactions observed in the structure, or predicted based on the structure, suggest opportunities for preparation of novel Sal analogs with improved potencies by use of semi-synthesis or by total synthesis.

The structure shows that the SalA residue-9 epoxide moiety is directed toward the RNAP secondary channel and RNAP active-center i+1 site (FIG. 3) but makes limited interactions with RNAP (FIG. 3). The SalA epoxide can be altered with little or no loss of activity (Tables 1-2), and has unique chemical reactivity (Examples 7-10). Accordingly, it is inferred herein that it should be possible—by semi-synthesis or by total synthesis—to append at the SalA residue-9 epoxide moiety by chemical functionality that makes favorable interactions with the RNAP secondary channel or active-center i+1 site, thereby increasing the potency of RNAP inhibitory activity and potentially increasing the potency of antibacterial activity.

The structure predicts that the SalB residue-9 chlorohydrin moiety likewise makes limited interactions with RNAP and is directed toward the RNAP secondary channel and RNAP active-center i+1 site and. The SalB chlorohydrin can be altered with little loss of activity (Tables 1-2), and has unique chemical reactivity (Example 11). Accordingly, it is inferred herein that it should be possible—by semi-synthesis or by total synthesis—to append at the SalB residue-9 chlorohydrin moiety chemical functionality that makes favorable interactions with the RNAP secondary channel or active-center i+1 site, thereby increasing the potency of RNAP inhibitory activity and potentially increasing the potency of antibacterial activity.

By way of example, appending—at the SalA residue-9 epoxide moiety or the SalB residue-9 chlorohydrin moiety—a sidechain that carries a nucleoside, a a nucleoside analog, or a nucleoside analog inhibitor able to bind to the RNAP active-center i+1 site could allow for favorable interactions with the RNAP active-center i+1 site, potentially enabling a very high potency of RNAP inhibitory activity and potentially a very high potency of antibacterial activity.

Example 2

Crystal Structure of RNAP in Complex with Sal Derivative

To confirm the binding position and binding orientation of Sal inferred from the crystal structure of RNAP-SalA, x-ray diffraction data and bromine anomalous scattering data were collected for crystals of *Escherichia coli* RNAP holoenzyme soaked with the bromine-containing Sal derivative Sal-Br (compound 3; crystal soaks, structure determination, and structure refinement performed essentially as described for SalA in Example 1). Sal-Br contained a residue-9 bromohydrin moiety analogous to the residue-9 chlorohydrin moiety of SalB, and was prepared by semi-synthesis from SalA, exploiting the chemical reactivity of the SalA residue-9 epoxide (Example 3). Sal-Br exhibited essentially full RNAP-inhibitory activity and antibacterial activity (Tables 1-2).

Electron density for Sal-Br from crystals of RNAP-Sal-Br complex matched electron density for SalA in the RNAP-SalA complex. Bromine anomalous difference density showed a single peak (FIG. 3). The peak was located adjacent to the electron density for Sal-Br, in the position predicted for the bromine atom of the Sal-Br residue-9 bromohydrin carbon atom (FIG. 3). The results unequivocally define the SalA and Sal-Br binding positions and binding orientations.

Example 3

Crystal Structure of Transcription Initiation Complex Containing Nucleoside Triphosphate Analog in RNAP Active-Center i+1 Site: Pre-Insertion Binding Mode A crystal structure of a transcription initiation complex containing a nucleoside triphosphate analog in the RNAP active-center i+1 in a pre-insertion-mode was obtained by soaking a pre-formed crystal of *Thermus thermophilus* RNAP-promoter open complex (RPo; DNA scaffold of Zhang et al., *Science* 338:1076-1080, 2012) with the first initiating nucleoside triphosphate (ATP) and a non-reactive analog of the second initiating nucleoside triphosphate (CMPcPP) (resolution=3.1 Å; FIG. 5).

Crystals were grown as described (Zhang et al., *Science* 338:1076-1080, 2012). Crystal soaking was performed by the addition of 0.1 µl 80 mM ATP (GE Healthcare, Inc.) and 0.1 µl 80 mM CMPcPP (Jena Biosciences, Inc.) in 60 mM Tris-HCl, pH 8.4, 120 mM KCl, 30 mM $MgCl_2$, and 5.7% PEG4000 to the crystallization drop and incubation 15 min at 25° C. Soaked crystals were transferred to reservoir solutions containing 17.5% (v/v) (2R,3R)-(-)-2,3-butanediol (Aldrich, Inc.) and then flash-cooled with liquid nitrogen. Diffraction data were collected from cryo-cooled crystals at Brookhaven National Laboratory beamline X25. Data were processed using HKL2000 and the structure was solved by molecular replacement in AutoMR, using PDB 4G7H as search model, refined in Phenix, and fitted in Coot.

The resulting electron density maps show unambiguous electron density for ATP in the RNAP active-center i site and for CMPcPP:$Mg^{2+}$(II) in the RNAP active-center i+1 site (FIG. 5B). CMPcPP is bound in a pre-insertion mode, in which the base moiety of CMPcPP base-pairs with the base of the DNA template-strand nucleotide in the i+1 site and stacks on the base of ATP in the i site, but in which the sugar and triphosphate moieties of CMPcPP do not engage the catalytic $Mg^{2+}$(I) ion, the active center is not dehydrated, and the trigger loop is not closed. (FIGS. 5C-D).

The CMPcPP γ phosphate is positioned adjacent to the entrance to the Sal target (FIG. 5D). There is a sterically unobstructed path between the CMPcPP γ phosphate and the Sal target.

Example 4

Crystal Structure of Transcription Initiation Complex Containing Nucleoside Triphosphate Analog in RNAP Active-Center i+1 Site: Insertion Binding Mode A crystal structure of a transcription initiation complex containing a nucleoside triphosphate analog in the RNAP active-center i+1 in a pre-insertion-mode was obtained by soaking a pre-formed crystal of *Thermus thermophilus* RPo (DNA scaffold of Zhang et al., *Science* 338:1076-1080, 2012) with a ribodinucleotide primer (GpA) and a non-reactive analog of the second initiating nucleoside triphosphate (CMPcPP) (resolution=3.1 Å; FIG. 6).

Crystal growth, crystal soaking, data collection, structure determination, and structure refinement were performed using the procedures of Example 3.

The resulting electron density maps show unambiguous electron density for GpA in the RNAP active-center i-1 and i sites and for CMPcPP:$Mg^{2+}$(II) in the RNAP active-center i+1 site (FIG. 6B). CMPcPP is bound in an insertion, or insertion-like, mode, in which the base moiety of CMPcPP base-pairs with the base of the DNA template-strand nucleotide in the i+1 site and stacks on the RNA 3' end in the i site, the sugar and triphosphate moieties of CMPcPP are re-oriented—rotated ~30° relative to their orientations in the pre-insertion-mode structure of Example 4—and make additional interactions, the active center is dehydrated, and the trigger loop is closed. (FIGS. 6C-D).

The CMPcPP γ phosphate is positioned close to the entrance to the Sal target (FIG. 6D). There is a sterically unobstructed path between the CMPcPP γ phosphate and the Sal target.

Example 5

Structural Model of Sal Bound to Sal Target and Nucleoside Triphosphate Analog Bound to RNAP Active-Center i+1 Site: Pre-Insertion Mode A structural model of Sal bound to the Sal target and a nucleoside triphosphate analog bound to the RNAP active-center i+1 site in a pre-insertion mode was prepared by superimposing the crystal structure of RNAP-SalA (Example 1) with the crystal structure of RPo-ATP-CMPcPP (Example 3) (FIG. 7).

The structural model indicates that distances between the SalA residue-9 epoxide moiety and the pre-insertion-mode nucleoside triphosphate analog Pγ, Pβ, Pα, and C5' atoms are, respectively, 6.8, 7.9, 8.4, and 10.8 Å (FIG. 7). The structural model further indicates that there are sterically unobstructed paths between the SalA residue-9 epoxide moiety and the pre-insertion-mode nucleoside triphosphate analog Pγ, Pβ, Pα, O5', and C5' atoms.

It is inferred that the SalA residue-9 epoxide moiety could be connected to the pre-insertion-mode nucleoside triphosphate analog Pγ, Pβ, Pα, O5', and C5' atoms through linkers comprising chains of, respectively, about 5 to about 10 consecutive atoms, about 6 to about 12 consecutive atoms, about 6 to about 12 consecutive atoms, and about 9 to about 18 consecutive atoms.

Example 6

Structural Model of Sal Bound to Sal Target and Nucleoside Triphosphate Analog Bound to RNAP Active-Center i+1 Site: Insertion Mode A structural model of Sal bound to the Sal target and a nucleoside triphosphate analog bound to the RNAP active-center i+1 site in an insertion mode was prepared by superimposing the crystal structure of RNAP-SalA (Example 1) with the crystal structure of RPo-GpA-CMPcPP (Example 4) (FIG. 8).

The crystal structure of RNAP in complex with SalA (Example 1) indicates that binding of SalA is likely to prevent full closure (fully folding) of the RENAP trigger loop (Example 1). Therefore, in structural modelling of Sal bound to the Sal target and a nucleoside triphosphate analog bound to the RNAP active-center i+1 site in an insertion mode, trigger loop residues that enter the RNAP active-center i+1 site only in a fully closed trigger loop state were omitted.

It has been proposed that isomerization of the pre-insertion-mode complex to the insertion-mode complex may involve an intermediate in which at least one of re-orientation of the nucleoside triphosphate and dehydration of the RNAP active-center, precedes closure of the trigger loop. Structural modelling of an insertion-mode complex omitting trigger loop residues that enter the i+1 site only in the fully closed trigger loop state may capturre properties of such an intermediate.

The structural model indicates that distances between the SalA residue-9 epoxide moiety and the insertion-mode nucleoside triphosphate analog Pγ, Pβ, Pα, and C5' atoms are, respectively, 8.6, 9.4, 8.7, and 10.2 Å (FIG. 8). The structural model further indicates that there are sterically unobstructed paths between the SalA residue-9 epoxide moiety and the insertion-mode nucleoside triphosphate analog Pγ, Pβ, Pα, O5', and C5' atoms.

It is inferred that the SalA residue-9 epoxide moiety could be connected to the insertion-mode nucleoside triphosphate analog Pγ, Pβ, Pα, O5', and C5' atoms through linkers comprising chains of, respectively, about 7 to about 14 consecutive atoms, about 7 to about 14 consecutive atoms, about 7 to about 14 consecutive atoms, and about 8 to about 16 consecutive atoms.

Example 7

Synthesis of Sal Derivatives Exploiting Reactivity of SalA Epoxide: Sal-Br (Compound 3)

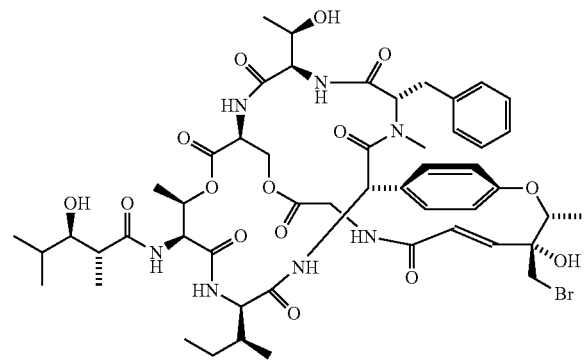

3

SalA (1; 5 mg; 4.9 μmol; prepared as in Trischman et al., *J. Am. Chem. Soc.,* 116:757, 1994; provided by William Fenical, Scripps Institution of Oceanography) was dissolved in 0.25 ml chloroform at 25° C. To the solution was added 48% HBr (10 μl, 89 μmol; Aldrich). The reaction mixture was stirred 15 min at 25° C., and then quenched with 200 μl 50% sodium bicarbonate. The organic layer was separated, re-washed with 100 μl water, and dried to a white solid. Products were purified using silica flash chromatography (0-10% methanol in chloroform as eluent).

Yield: 5 mg, 93%.

MS (MALDI): calculated: m/z 1099.41, 1101.41. found: 1122.48, 1124.48 (M+Na$^+$).

Example 8

Synthesis of Sal Derivatives Exploiting Reactivity of SalA Epoxide: Sal-OH (Compound 4)

4

SalA (1; 1 mg; 0.98 μmol; prepared as in Trischman et al., *J. Am. Chem. Soc.,* 116:757, 1994; provided by William Fenical, Scripps Institution of Oceanography) was dissolved in 0.5 ml n-butanol, and 1 μl 98% sulfuric acid was added. The reaction mixture was heated 10 min at 100° C. in a microwave reactor (Initiator, Biotage, Inc.), cooled to 25° C., and then neutralized with 400 μl 50% sodium bicarbonate. The organic layer was retrieved and evaporated to dryness. Products were purified by reversed-phase HPLC [Luna C18, 5μ, 100 A, 250 mm×4.6 mm (Phenomenex, Inc.); A, 60% methanol; B, 75% methanol; 0-15 min, 0% B; 15-30 min, 0-100% B; flow rate 1 ml/min)]. Compound 4 eluted at 38 min. Yield: 80 μg, 7.7%.

MS (MALDI): calculated: m/z 1037.50. found: 1060.50 (M+Na$^+$).

Example 9

Synthesis of Sal Derivatives Exploiting Reactivity of SalA Epoxide: Sal-OR 9.1. Sal-OBu A (compound 5A) and Sal-OBu B (Compound 5B)

5A

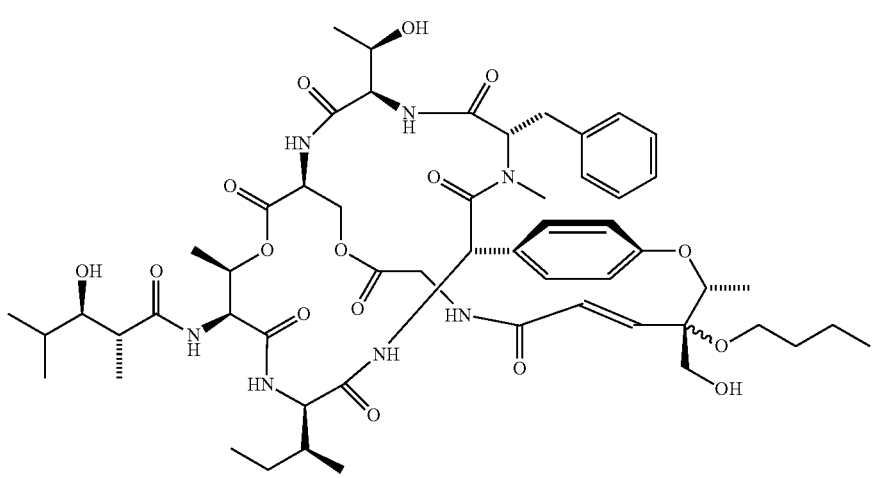

5B

Ole;2qSalA (1; 1 mg; 0.98 μmol; prepared as in Trischman et al., *J. Am. Chem. Soc.*, 116:757, 1994; provided by William Fenical, Scripps Institution of Oceanography) was dissolved in 0.5 ml n-butanol, and 1 μl 98% sulfuric acid was added. The reaction mixture was heated 10 min at 100° C. in a microwave reactor (Initiator, Biotage, Inc.), cooled to 25° C., and then neutralized with 400 μl 50% sodium bicarbonate. The organic layer was retrieved and evaporated to dryness. Products were purified by reversed-phase HPLC [Luna C18, 5μ, 100 Å, 250 mm×4.6 mm (Phenomenex, Inc.); A, 60% methanol; B, 75% methanol; 0-15 min, 0% B; 15-30 min, 0-100% B; flow rate 1 ml/min)]. Compound 5A eluted at 56 min. Compound 5B eluted at 53 min.

Compound 5A: Yield: 140 μg, 9%. MS (MALDI): calculated: m/z 1093.62. found: 1094.63, 1116.59 (M+Na⁺).

Compound 5B: Yield: 69 μg, 4.4%. MS (MALDI): calculated: m/z 1093.62. found: 1094.63, 1116.59 (M+Na⁺).

Example 10

Synthesis of Sal Derivatives Exploiting Reactivity of SalA Epoxide: Sal-SR 10.1. Sal-SBu (Compound 6)

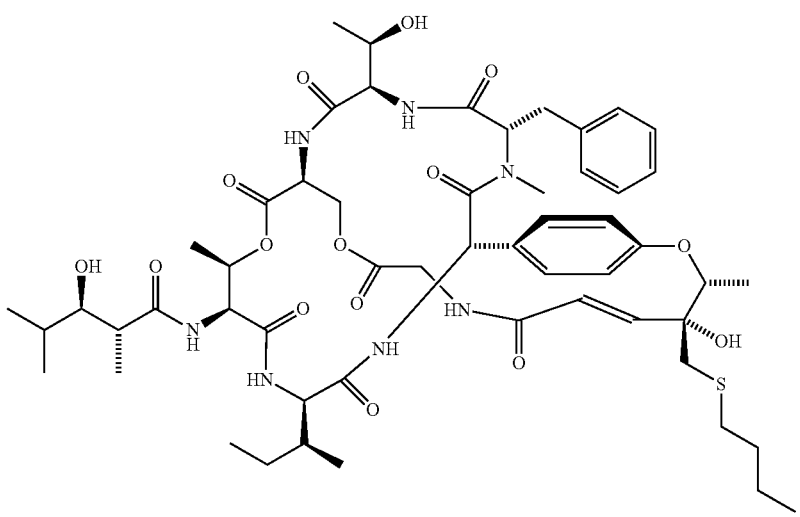

6

Compound 6 is prepared as described for compound 5A, except that 0.5 ml benzene, 5 μmol lithium perchlorate, and 10 μmol butanethiol are used in place of 0.5 ml n-butanol, and 1 μl 98% sulfuric acid.

Example 11

Synthesis of Sal Derivatives Exploiting Reactivity of SalB Chlorohydrin: Sal-NHR 11.1. Sal-NH(CH$_2$)$_3$NHBoc (Compound 7)

heated 5 min at 150° C. in a microwave reactor (Initiator; Biotage, Inc.), cooled to 25° C., and then evaporated to dryness. Products were purified by reversed-phase HPLC [Luna C18, 5 μ, 100 A, 250 mm×4.6 mm (Phenomenex, Inc.); A, 60% methanol; B, 75% methanol; 0-15 min, 0% B; 15-30 min, 0-100% B; flow rate 1 ml/min)]. Compound 7 eluted at 35 min.

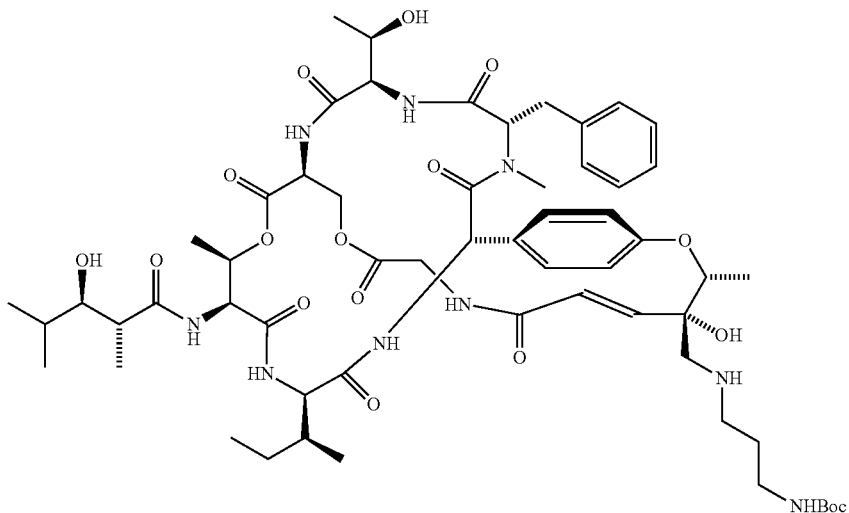

7

SalB (2; 5 mg; 4.7 μmol; prepared as in Trischman et al., *J. Am. Chem. Soc.*, 116:757, 1994; provided by William Fenical, Scripps Institution of Oceanography) was dissolved in 1 ml ethanol, and N-Boc-1,3-diaminopropane (3.4 mg, 19.5 μmol; Aldrich, Inc.) was added. The reaction mixture was Yield: 0.261 mg, 4.5%.

MS (MALDI): calculated: m/z 1193.39. found: 1216.71 (M+Na$^+$).

11.2. Sal-NH(CH$_2$)$_3$NHBoc (Compound 8)

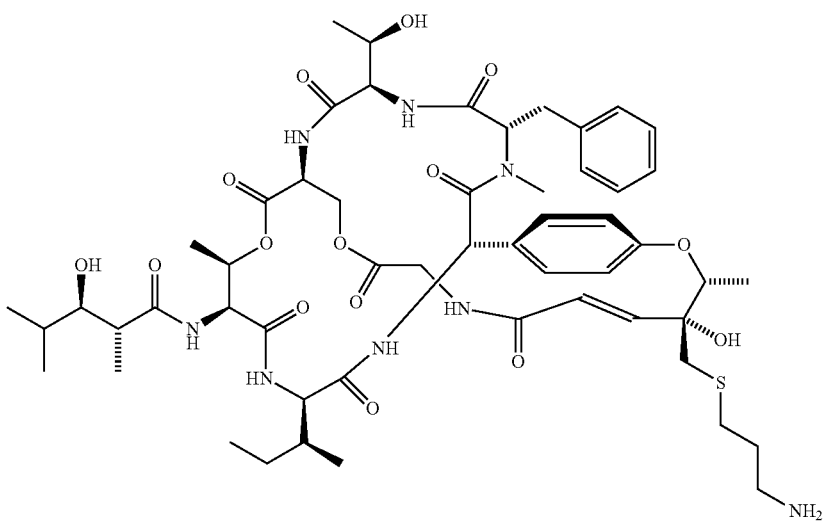

8

Compound 8 is prepared from compound 7 by reaction with 50 μl trifluoroacetic acid in 200 μl chloroform for 30 min at 25° C. and is purified by reversed-phase HPLC.

11.3. Sal-NH(CH$_2$)$_6$NHBoc (Compound 9)

ness. Products were purified by reversed-phase HPLC [Luna C18, 5μ, 100 A, 250 mm×4.6 mm (Phenomenex, Inc.); A, 60% methanol; B, 75% methanol; 0-15 min, 0% B; 15-30 min, 0-100% B; flow rate 1 ml/min)]. Compound 8 eluted at 39 min.

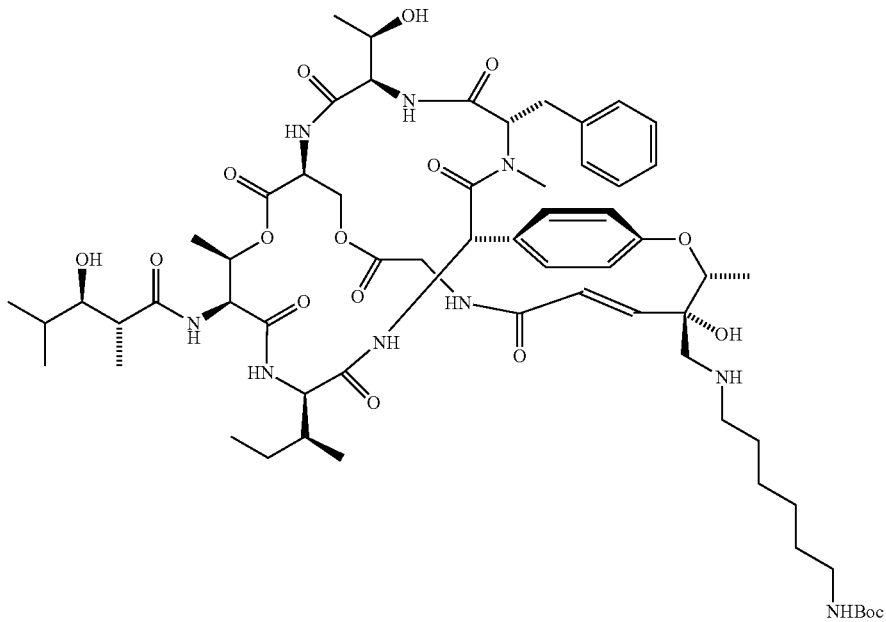

9

SalB (2; 10 mg; 9.5 μmol; prepared as in Trischman et al., J. Am. Chem. Soc., 116:757, 1994; provided by William Fenical, Scripps Institution of Oceanography) was dissolved in 1 ml ethanol, and N-Boc-1,6-diaminohexane (4.1 mg, 18.95 μmol; Acros, Inc.) was added. The reaction mixture was heated 6 min at 160° C. in a microwave reactor (Initiator; Biotage, Inc.), cooled to 25° C., and then evaporated to dryness.

Yield: 1.46 mg, 14%.

MS (MALDI): calculated: m/z 1235.67. found: 1236.56 (M+H$^+$), 1258.58 (M+Na$^+$).

11.4. Sal-NH(CH$_2$)$_6$NHBoc (Compound 10)

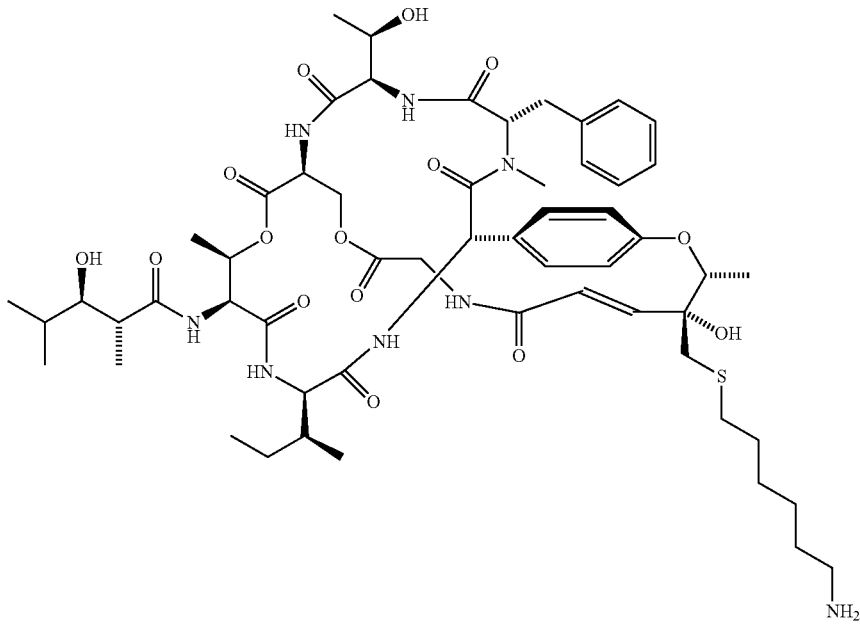

10

Compound 10 is prepared from compound 9 by reaction with 50 µl trifluoroacetic acid in 200 µl chloroform for 30 min at 25° C. and is purified by reversed-phase HPLC.

Example 12

Synthesis of Sal-(Nucleoside-Triphosphate) Conjugates

Sal-X(CH$_2$)$_n$NH$_2$ (X=O, S, or NH; n=2-8; can be prepared as in Examples 9-11; 1 pump can be reacted with uridine triphosphate (1 µmol) and dicyclohexylcarbodiimide (2 µmol) in 0.5 ml DMSO for 18 h at 37° C. to provide the corresponding Sal-(nucleoside-triphosphate) conjugates. Reactions are terminated by addition of water, and products are purified by reversed-phase HPLC.

Analogous procedures, optionally involving protection of base amines or other potentially reactive groups by methods known in the art, enable preparation of corresponding adenosine-triphosphate, guanosine-triphosphate, cytidine-triphosphate, and other nucleoside-triphosphate conjugates.

Example 13

Synthesis of Sal-Nucleoside Conjugates

Sal-X(CH$_2$)$_n$NH$_2$ (X=O, S, or NH; n=2-8; can be prepared as in Examples 9-11; 1 µmol) can be reacted with 5'-[HOOC(CH$_2$)$_3$CONH]-5'-deoxy-uridine [prepared from 5'-amino-5'-deoxy-2',3'-O-methylethylidene-uridine by reaction with glutaric acid and N,N-dicyclohexylcarbodiimide in dimethylformamide, followed by deprotection with 0.1 M HCl] and N,N-dicyclohexylcarbodiimide (10 µmol) in 0.5 ml dimethylformide for 18 h at 25° C. to provide the corresponding Sal-nucleoside conjugates. Reactions are terminated by addition of water, and products are purified by reversed-phase HPLC.

Analogous procedures, optionally involving protection of base amines or other, potentially reactive groups by methods known in the art, enable preparation of corresponding adenosine, guanosine, cytidine, and other nucleoside conjugates.

Example 14

RNAP-Inhibitory Activity

Radiochemical RNAP assays with *Escherichia coli* RNAP and *Staphylococcus aureus* RNAP were performed as follows: Reaction mixtures contained (10 µl): 0-100 µM test compound, bacterial RNAP holoenzyme [75 nM *Escherichia coli* RNAP holoenzyme (prepared as in Mukhopadhyay et al., *Meths. Enzymol.* 371:144-159, 2003) or 75 nM *Staphylococcus aureus* RNAP core enzyme and 300 nM *Staphylococcus aureus* σ$^A$ (prepared as in Srivastava et al., *Curr. Opin. Microbiol.* 14:532-543, 2011)], 20 nM DNA fragment N25-lacUV5-14 [positions −100 to −1 of the bacteriophage T5 N25 promoter followed by positions +1 to +29 of the lacUV5 (+10A; +15C) promoter; prepared by PCR amplification of a synthetic nontemplate-strand oligodeoxyribonucleotide], 0.5 mM ApA, 100 µM [α$^{32}$P]UTP (0.2 Bq/fmol), 100 µM ATP, and 100 µM GTP in TB (50 mM Tris-HCl, pH 7.9, 100 mM KCl, 10 mM MgCl$_2$, 1 mM DTT, 100 µg/ml bovine serum albumin, and 5% glycerol). Reaction components except DNA, ApA, and NTPs were pre-incubated 10 min at 24° C.; DNA was added and reaction mixtures were incubated 10 min at 37° C.; ApA, 0.15 µl 7 µM [α$^{32}$1]UTP (200 Bq/fmol), ATP, and GTP were added and reaction mixtures were incubated 5 min at 37° C.; and 0.5 µl 2 mM UTP was added and reaction mixtures were incubated 5 min at 37° C. Reactions were terminated by adding 10 µl loading buffer (80% formamide, 10 mM EDTA, 0.02% bromophenol blue, and 0.02% xylene cyanol) and heating 2 min at 95° C. Products were applied to 7 M urea 15% polyacrylamide (19:1 acrylamide:bisacrylamide) slab gels (Bio-Rad), electrophoresed in TBE (90 mM Tris-borate, pH 8.0, and 2 mM EDTA), and analyzed by storage-phosphor scanning (Typhoon; GE Healthcare, Inc.).

Radiochemical assays with human RNAP I, II, and III were performed essentially as described [Sawadogo and Roeder, *Cell* 43:165-75, 1985]. Reaction mixtures contained (20 µl): 0-100 µM test compound, 8 U HeLaScribe Nuclear Extract (Promega, Inc.), 1 µg human placental DNA (Sigma-Aldrich), 400 µM ATP, 400 µM [α$^{32}$P]UTP (0.11 Bq/fmol), 400 µM CTP, 400 µM GTP, 50 mM Tris-HCl, pH 8.0, 7 mM HEPES-NaOH, 70 mM (NH$_4$)$_2$SO$_4$, 50 mM KCl, 12 mM MgCl$_2$, 5 mM DTT, 0.1 mM EDTA, 0.08 mM phenylmethylsulfonyl fluoride, and 16% glycerol. Reaction components other than DNA and NTPs were pre-incubated 10 min at 30° C., DNA was added and reaction mixtures were incubated 15 min at 30° C., NTPs were added and reaction mixtures were incubated 60 min at 30° C. Reaction mixtures were spotted on DE81 filter discs (Whatman, Inc.; pre-wetted with water) and incubated 1 min at room temperature. Filters were washed with 3×3 ml Na$_2$HPO$_4$, 2×3 ml water, and 3 ml ethanol, using a filter manifold (Hoefer, Inc.). Filters were placed in scintillation vials containing 10 ml Scintiverse BD Cocktail (Thermo Fisher, Inc.), and radioactivity was quantified by scintillation counting (LS6500; Beckman-Coulter, Inc.).

Fluorescence-detected RNAP assays with *Escherichia coli* RNAP were performed by a modification of the procedure of Kuhlman et al., 2004 [Kuhlman et al., *Anal. Biochem.* 324: 183-190, 2004]. Reaction mixtures contained (20 µl): 0-100 nM test compound, 75 nM *Escherichia coli* RNAP σ$^{70}$ holoenzyme, 20 nM 384 by DNA fragment containing the bacteriophage T4 N25 promoter, 100 µM ATP, 100 µM GTP, 100 µM UTP, 100 µM CTP, 50 mM Tris-HCl, pH 8.0, 100 mM KCl, 10 mM MgCl$_2$, 1 mM DTT, 10 µg/ml bovine serum albumin, and 5.5% glycerol. Reaction components other than DNA and NTPs were pre-incubated for 10 min at 37° C. Reactions were carried out by addition of DNA and incubation for 5 min at 37° C., followed by addition of NTPs and incubation for 60 min at 37° C. DNA was removed by addition of 1 µl 5 mM CaCl$_2$ and 2 U DNaseI (Ambion, Inc.), followed by incubation for 90 min at 37° C. RNA was quantified by addition of 100 µl RiboGreen RNA Quantitation Reagent (Invitrogen, Inc.; 1:500 dilution in Tris-HCl, pH 8.0, 1 mM EDTA), followed by incubation for 10 min at 25° C., followed by measurement of fluorescence intensity [excitation wavelength=485 nm and emission wavelength=535 nm; QuantaMaster QM1 spectrofluorometer (PTI, Inc.)].

Half-maximal inhibitory concentrations (IC50s) were calculated by non-linear regression in SigmaPlot (SPSS, Inc.).

Example 15

Antibacterial Activity

Antibacterial activity was quantified using broth microdilution [Clinical and Laboratory Standards Institute (CLSUNCCLS), *Methods for Dilution Antimicrobial Susceptibility Tests for Bacteria That Grow Aerobically; Approved Standard, Eighth Edition. CLIS Document M07-A8* (CLIS, Wayne Pa.), 2009]. Assays with *Enterobacter cloacae* ATCC 13047, *Pseudomonas aeruginosa* ATCC10145, and *Escheri*- chia coli D21f2to1C, employed a starting cell density of 2-5×10⁵ cfu/ml, Mueller Hinton II cation adjusted broth (BD Biosciences, Inc.), and an air atmosphere. Assays with *Haemophilus influenzae* ATCC49247 and *Neisseria gonorrhoeae* ATCC 19424 employed a starting cell density of $2-5 \times 10^5$ cfu/ml, Haemophilus Test Medium broth (Barry et al., 1993) and a 5% CO2/95% air atmosphere. MIC50 was defined as the minimal concentration resulting in ≥50% inhibition of bacterial growth.

Example 16

Cytotoxicity

MICs for mammalian cells (Vero E6) in culture were quantified using CellTiter96 assay (Promega. Inc.; procedures as specified by the manufacturer). Screening data for SalA and SalB (compounds 1 and 2) and representative compounds of this invention (compounds 3-9) are presented in Tables 1-2:

TABLE 1

RNAP-inhibitory activity (fluorescent-detected RNAP assays)

| compound | IC50 Escherichia coli RNAP (μM) | IC50 human RNAP I/II/III (μM) |
| --- | --- | --- |
| SalA (1) | 1 | >100 |
| SalB (2) | 1 | >100 |
| Sal-Br (3) | 3 | >100 |
| Sal-OH (4) | 2 | |
| Sal-OBu A (5A) | 6 | |
| Sal-OBu B (5B) | >25 | |
| Sal-NH(CH₂)₃NHBoc (7) | 0.6 | |
| Sal-NH(CH₂)₆NHBoc (9) | 1 | |

TABLE 2

Antibacterial activity

| compound | MIC50 Escherichia coli D21f2toIC (μg/ml) | MIC50 Enterobacter cloacae ATCC 13047 (μg/ml) |
| --- | --- | --- |
| SalA (1) | 0.024 | 1.56 |
| SalB (2) | 0.098 | 6.25 |
| Sal-Br (3) | 0.049 | 1.56 |
| Sal-OH (4) | 0.78 | 25 |
| Sal-OBu A (5A) | 1.56 | 12.5 |
| Sal-NH(CH₂)₃NHBoc (7) | 1.56 | 100 |
| Sal-NH(CH₂)₆NHBoc (9) | 0.78 | 25 |

TABLE 3

Absence of cytotoxicity to mammalian cells in culture

| compound | MIC50 Vero E6 ATCC CRL1586 (μg/ml) |
| --- | --- |
| SalA (1) | >100 |
| SalB (2) | >100 |
| Sal-Br (3) | >100 |

All documents cited herein are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. A compound of formula (I):

X-α-Y (I)

wherein:

X is a moiety that binds to the salinamide binding site of a bacterial RNA polymerase;

Y is a nucleoside, a singly phosphorylated nucleoside, or a multiply phosphorylated nucleoside; and α is a linker;

or a salt thereof.

2. The compound of claim 1, wherein X is:

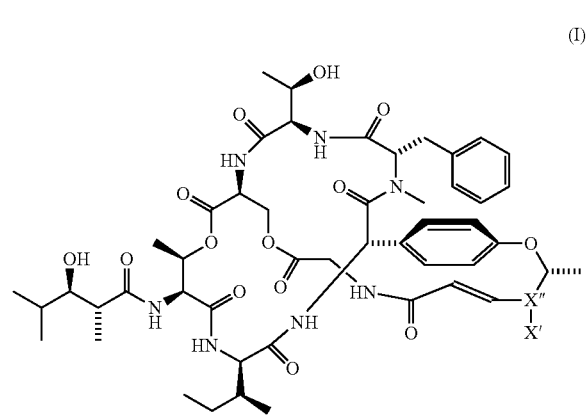

(I)

wherein:

one of X' and X" is the point of attachment of α and the other of X' and X" is a carbon atom substituted with —OH.

3. The compound of claim 1, wherein X is formula (Ia):

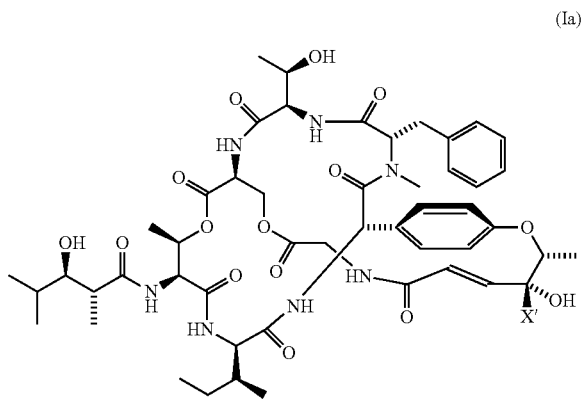

and wherein X' is the point of attachment of α.

4. The compound of claim 1, wherein X is a salinamide.

5. The compound of claim 1, wherein Y is a nucleoside inhibitor of a bacterial RNA polymerase.

6. The compound of claim 1, wherein α comprises a chain of about 0 to about 25 consecutively bonded atoms.

7. The compound of claim 1, wherein α comprises a chain of about 0 to about 25 consecutively bonded atoms and in which the atom attached to X is one of O, S, and $NR^a$, wherein $R^a$ is H or $C_1$-$C_4$ alkyl.

8. The compound of claim 1, wherein α comprises a chain of about 0 to about 25 consecutively bonded atoms and in which the atom attached to Y is one of O, S, $NR^a$, and C(=O), wherein $R^a$ is H or $C_1$-$C_4$ alkyl.

9. The compound of claim 1, wherein α comprises a chain of about 0 to about 25 consecutively bonded atoms and in which the atoms attached to X and Y each independently are one of O, S, $NR^a$, and C(=O), wherein $R^a$ is H or $C_1$-$C_4$ alkyl.

10. The compound of claim 1 that binds to a bacterial RNA polymerase.

11. The compound of claim 1 that binds to a bacterial RNA polymerase with an affinity higher than the affinity of X and the affinity of Y.

12. The compound of claim 1 that inhibits a bacterial RNA polymerase.

13. The compound of claim 1 that inhibits a bacterial RNA polymerase with a potency higher than the potency of X and the potency of Y.

14. The compound of claim 1 that inhibits a bacterial RNA polymerase resistant to at least one of X and Y.

15. The compound of claim 1, wherein said compound is prepared from precursors X-α' and 'α-Y, where α' and 'α are moieties that can react to form α.

16. The compound of claim 1, wherein said compound is prepared from precursors X-α' and 'α-Y, where α' and 'α are moieties that can react to form α, and wherein said compound is prepared from precursors X-α' and 'α-Y in the presence of a bacterial RNA polymerase.

17. A method of preparation of a compound of claim 1, comprising: 1) reaction of a salinamide derivative containing one of an epoxide and a halide with a compound containing one of HO(CH$_2$)$_n$N(R)Z, HS(CH$_2$)$_n$N(R)Z, and HN(R')(CH$_2$)$_n$N(R)Z', wherein n is 2, 3, 4, 5, 6, 7, or 8, R and R' each independently is one of H and $C_1$-$C_4$ alkyl, and Z is H or a protecting group, to provide a synthetic intermediate; and 2) reaction of the synthetic intermediate with a precursor α'-Y containing one of a carboxyl, an activated ester, and an anhydride to provide the compound of claim 1.

18. A method of preparation of a compound of claim 1, comprising: 1) reaction of a precursor α'-Y containing one of a carboxyl, an activated ester, and an anhydride with a compound containing one of HN(R)(CH$_2$)$_n$OZ, of HN(R)(CH$_2$)$_n$SZ, and HN(R)(CH$_2$)$_n$N(R)Z, wherein n is 2, 3, 4, 5, 6, 7, or 8, R and R' each independently is one of H and $C_1$-$C_4$ alkyl, and Z is H or a protecting group, to provide a synthetic intermediate; and 2) reaction of the synthetic intermediate with a precursor α'-X containing one of an epoxide and a halide to provide the compound of claim 1.

19. A pharmaceutical composition comprising a compound of formula (I) as described in claim 1, or a pharmaceutically acceptable salt thereof, and a pharmaceutically acceptable carrier.

20. The compound of claim 1, wherein Y is a nucleoside triphosphate.

21. The compound of claim 1, wherein Y is a nucleoside triphosphate, and wherein the point of attachment of α to the nucleoside triphosphate is an atom of the γ phosphate of the nucleoside triphosphate.

22. The compound of claim 20, wherein α is one of —O(CH$_2$)$_n$N(R)—, —S(CH$_2$)$_n$N(R)—, and —N(R)(CH$_2$)$_n$N(R')—, wherein each n is independently 2, 3, 4, 5, 6, 7, or 8, and each R and R' independently is one of H and $C_1$-$C_4$ alkyl.

23. The compound of claim 21, wherein α is one of —O(CH$_2$)$_n$N(R)—, —S(CH$_2$)$_n$N(R)—, and —N(R)(CH$_2$)$_n$N(R)—, wherein each n is independently 3, 4, 5, or 6, and each R and R' independently is one of H and $C_1$-$C_4$ alkyl.

24. The compound of claim 1, wherein Y is a ribonucleoside.

25. The compound of claim 1, wherein Y is a ribonucleoside, and wherein the point of attachment of α to the ribonucleoside is one of the O5' atom and the C5' atom of the ribonucleoside or ribonucleoside derivative.

26. The compound of claim 24, wherein α is one of —O(CH$_2$)$_n$—N(R)—, —S(CH$_2$)$_n$NH—, —N(R)(CH$_2$)$_n$N(R')—, —O(CH$_2$)$_n$N(R')C(O)(CH$_2$)$_{n'}$N(R")—, —S(CH$_2$)$_{n'}$N(R)C(O)(CH$_2$)$_{n'}$N(R")—, and —N(R)(CH$_2$)$_n$N(R')C(O)(CH$_2$)$_{n'}$N(R")—, wherein n is 6, 7, 8, 9, 10, 11, or 12, n' is 2, 3, 4, 5, 6, 7, or 8, n" is 2, 3, or 4, and each R, R', and R" independently is one of H and $C_1$-$C_4$ alkyl.

27. The compound of claim 25, wherein α is one of —O(CH$_2$)$_n$N(R)—, —S(CH$_2$)$_n$NH—, —N(R)(CH$_2$)$_n$N(R)—, —O(CH$_2$)$_n$N(R')C(O)(CH$_2$)$_{n'}$N(R")—, —S(CH$_2$)$_{n'}$N(R)C(O)(CH$_2$)$_{n'}$N(R")—, and —N(R)(CH$_2$)$_n$N(R)C(O)(CH$_2$)$_{n'}$N(R")—, wherein n is 7, 8, 9, or 10, n' is 3, 4, 5, or 6, n" is 2, 3, or 4, and each R, R', and R" independently is one of H and $C_1$-$C_4$ alkyl.

28. The method of claim 17 wherein the synthetic intermediate is selected from:

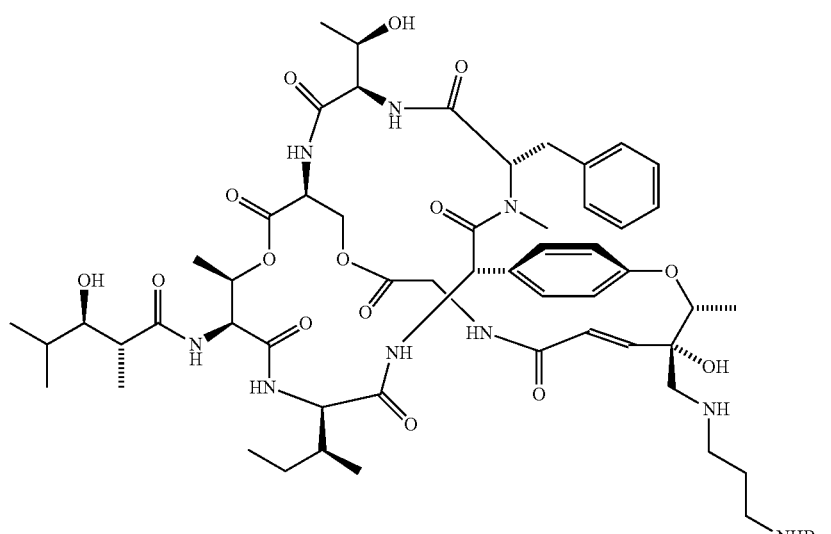
7
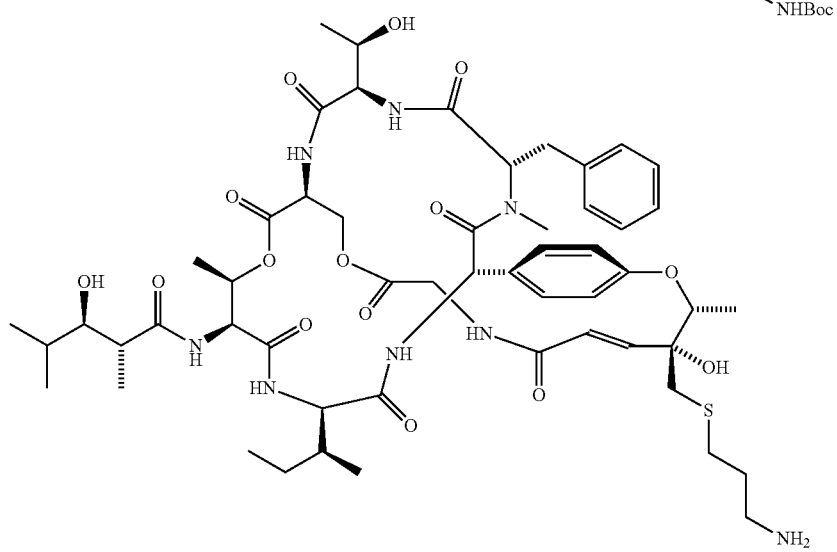
8
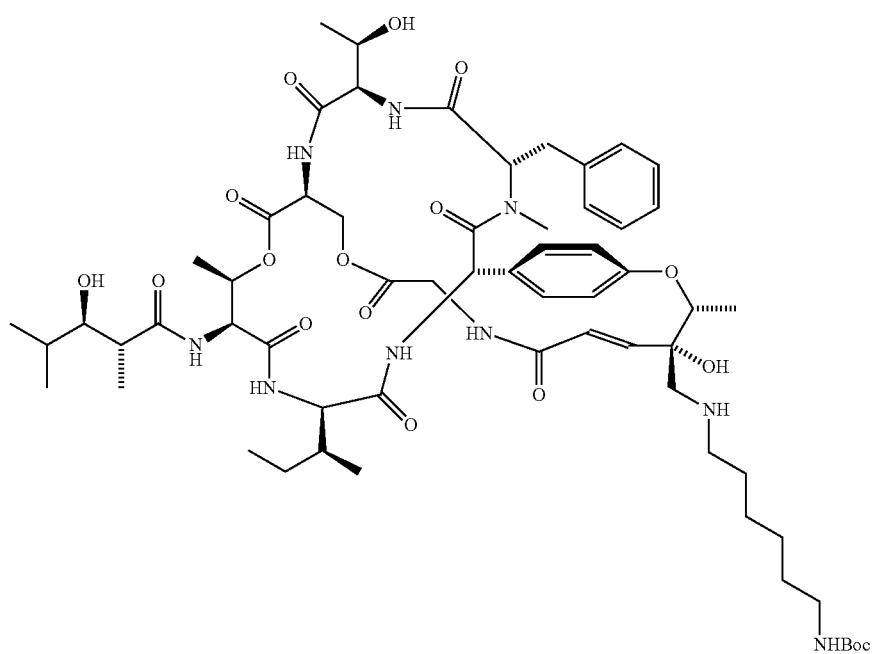
9
and

-continued

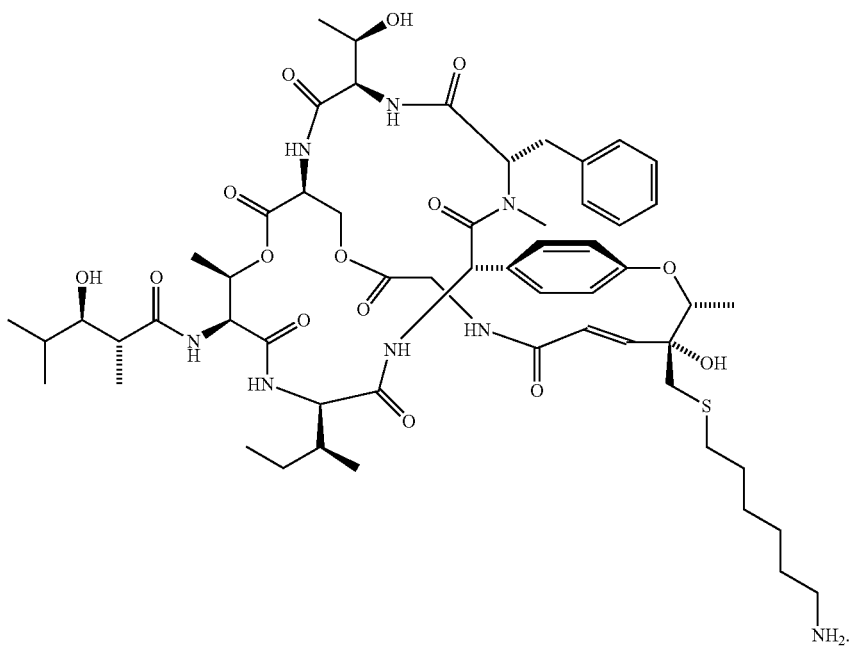

10

29. A method to inhibit a bacterial RNA polymerase comprising contacting a bacterial RNA polymerase with a compound of formula (I) as described in claim 1, or a salt thereof.

30. A method to treat a bacterial infection in an animal comprising administering a compound of formula (i) as described in claim 1, or a pharmaceutically acceptable salt thereof, to the animal.

* * * * *